United States Patent
Ye et al.

(10) Patent No.: US 9,695,208 B2
(45) Date of Patent: Jul. 4, 2017

(54) SIALIC ACID (A-(2-6))-D-AMINOPYRANOSE DERIVATIVES, SYNTHESIS METHODS AND USES THEREOF

(75) Inventors: Xinshan Ye, Beijing (CN); Fan Yang, Beijing (CN); Xiujing Zheng, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 378 days.

(21) Appl. No.: 13/703,007

(22) PCT Filed: Apr. 8, 2011

(86) PCT No.: PCT/CN2011/000610
§ 371 (c)(1),
(2), (4) Date: Dec. 7, 2012

(87) PCT Pub. No.: WO2011/153815
PCT Pub. Date: Dec. 15, 2011

(65) Prior Publication Data
US 2013/0079291 A1    Mar. 28, 2013

(30) Foreign Application Priority Data
Jun. 9, 2010  (CN) .......................... 2010 1 0202388

(51) Int. Cl.
| | | |
|---|---|---|
| C07H 15/10 | (2006.01) | |
| C07H 15/04 | (2006.01) | |
| C07H 13/00 | (2006.01) | |
| A61K 47/48 | (2006.01) | |
| C07K 1/107 | (2006.01) | |
| C07K 2/00 | (2006.01) | |
| A61K 39/00 | (2006.01) | |

(52) U.S. Cl.
CPC .......... *C07H 13/00* (2013.01); *A61K 39/0011* (2013.01); *A61K 47/48092* (2013.01); *A61K 47/48284* (2013.01); *C07H 15/04* (2013.01); *C07H 15/10* (2013.01); *C07K 1/1077* (2013.01); *C07K 2/00* (2013.01); *A61K 2039/585* (2013.01); *A61K 2039/6081* (2013.01)

(58) Field of Classification Search
None
See application file for complete search history.

(56) References Cited

U.S. PATENT DOCUMENTS

2009/0324619 A1* 12/2009 Hwang et al. ............ 424/178.1

FOREIGN PATENT DOCUMENTS

| CN | 1543350  A | 11/2004 |
|---|---|---|
| WO | 9529927  A2 | 11/1995 |

OTHER PUBLICATIONS

International Search Report for PCT/CN2011/000610.
Yang Fan et al., Enhancement of the Immunogenicity of Synthetic Carbohydrate Vaccines by Chemical Modifications of STn Antigen, ACS Chemical Biology, Mar. 18, 2011, vol. 6, No. 3, pp. 252-259, Figures 1-3.
Sahabuddin SK et al., Synthesis of N-modified sTn analogs and evaluation of their immunogenicities by microarray-based immunoassay, Sep. 18, 2010, vol. 66, No. 38, pp. 7510-7519, compound 19.
Reddish Mark A. et al., Specificities of anti-sialyl-Tn and anti-Tn monoclonal antibodies generated using novel clustered synthetic glycopeptide epitopes, Glycoconjugate Journal, 1997, vol. 14, No. 5, pp. 549-560, see compounds (4)-(8) on p. 551.

* cited by examiner

*Primary Examiner* — Traviss C McIntosh, III
(74) *Attorney, Agent, or Firm* — The PL Law Group, PLLC

(57) ABSTRACT

N-acyl modified sialic acid ($\alpha$-(2→6))-D-aminopyranose derivatives, their synthesis methods and uses are disclosed. Sialic acid ($\alpha$-(2→6))-D-aminopyranose derivatives represented by formula 1 are synthesized by using D-aminogalactose (glucose) and sialic acid as raw materials, which are coupled with carrier proteins or polypeptides to obtain glycoprotein (glycopeptide) conjugates. Acetyl is replaced by derivative acyl in the structures of said compounds, therefore the compounds show good activity in antitumor vaccines.

10 Claims, 4 Drawing Sheets

Formula ( I )

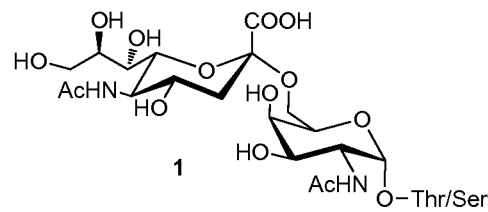
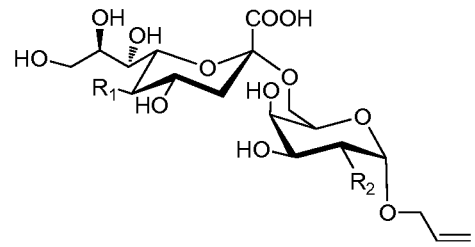

2 $R_1=R_2=AcNH$
3 $R_1=EtCONH, R_2=AcNH$
4 $R_1=n\text{-PrCONH}, R_2=AcNH$
5 $R_1=i\text{-PrCONH}, R_2=AcNH$
6 $R_1=n\text{-PenCONH}, R_2=AcNH$
7 $R_1=CH_2FCONH, R_2=AcNH$
8 $R_1=CHF_2CONH, R_2=AcNH$
9 $R_1=CF_3CONH, R_2=AcNH$
10 $R_1=CH_2ClCONH, R_2=AcNH$
11 $R_1=CHCl_2CONH, R_2=AcNH$
12 $R_1=CCl_3CONH, R_2=AcNH$

13 $R_1=N_3, R_2=AcNH$
14 $R_1=NH_2, R_2=AcNH$
15 $R_1=CH_2BrCONH, R_2=AcNH$
16 $R_1=AcNH, R_2=EtCONH$
17 $R_1=AcNH, R_2=n\text{-PrCONH}$
18 $R_1=AcNH, R_2=i\text{-PrCONH}$
19 $R_1=AcNH, R_2=n\text{-PenCONH}$
20 $R_1=AcNH, R_2=CH_2FCONH$
21 $R_1=AcNH, R_2=CHF_2CONH$
22 $R_1=AcNH, R_2=CF_3CONH$
23 $R_1=AcNH, R_2=CH_2ClCONH$
24 $R_1=AcNH, R_2=CHCl_2CONH$

25 $R_1=AcNH, R_2=N_3$
26 $R_1=AcNH, R_2=NH_2$
27 $R_1=R_2=EtCONH$
28 $R_1=R_2=n\text{-PrCONH}$
29 $R_1=R_2=i\text{-PrCONH}$
30 $R_1=R_2=n\text{-PenCONH}$
31 $R_1=R_2=CH_2FCONH$
32 $R_1=R_2=CHF_2CONH$
33 $R_1=R_2=CF_3CONH$
34 $R_1=R_2=CH_2ClCONH$
35 $R_1=R_2=CH_2Cl_2CONH$
36 $R_1=R_2=CCl_3CONH$

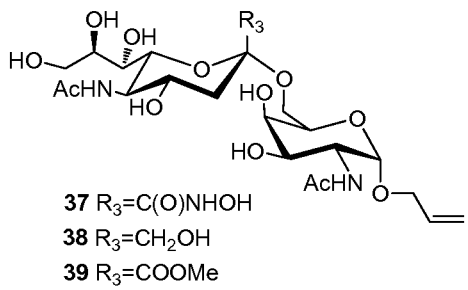

37 $R_3=C(O)NHOH$
38 $R_3=CH_2OH$
39 $R_3=COOMe$

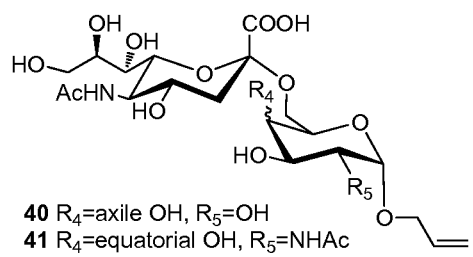

40 $R_4$=axile OH, $R_5$=OH
41 $R_4$=equatorial OH, $R_5$=NHAc

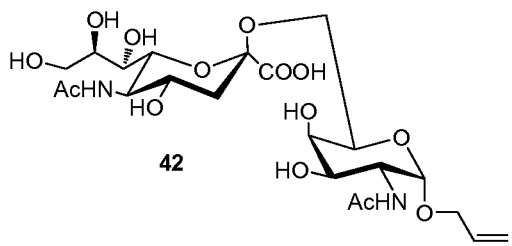
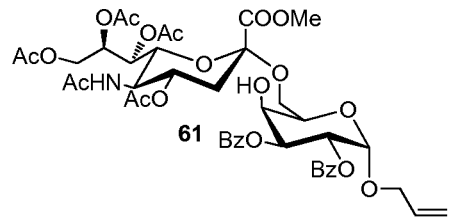
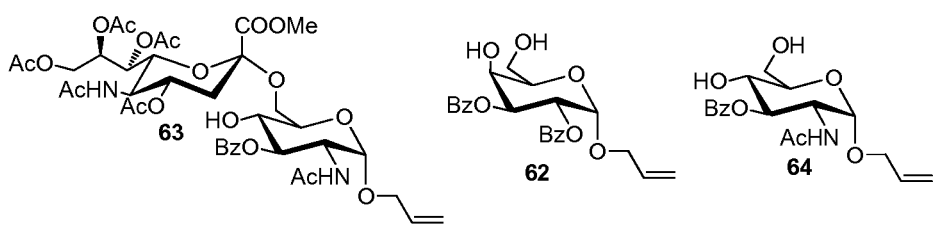

Fig. 2

SIALIC ACID (A-(2-6))-D-AMINOPYRANOSE DERIVATIVES, SYNTHESIS METHODS AND USES THEREOF

CROSS REFERENCE TO RELATED APPLICATIONS AND CLAIM OF PRIORITY

This patent application is a National Phase application under 35 U.S.C. §371 of International Application No. PCT/CN2011/000610, filed on Apr. 8, 2011, entitled SIALIC ACID (α-(2→6))-D-AMINOPYRANOSE DERIVATIVES, SYNTHESIS METHODS AND USES THEREOF, which claims priority to Chinese Patent Application number 201010202388.5, filed on Jun. 9, 2010, entire contents of which are incorporated herein by reference.

BACKGROUND OF THE INVENTION

1. Field of the Invention

The present invention relates to the glycoconjugates, the sialic acid (α-(2→6))-D-aminopyranose derivatives, their conjugates to proteins or polypeptides and the synthesis methods thereof are of particular interest. And the present invention also relates to the application of these compounds in the preparation of anti-tumor drugs. The present invention falls within the area of anti-tumor vaccines.

2. Description of the Background Art

In recent years, vaccines based on the tumor-associated carbohydrate antigens (TACAs) are regarded as one of the research hotspots. STn antigen, a sialic acid-containing disaccharide, is expressed abundantly on breast, prostate, pancreas, colorectal, lung, gastric, and ovarian cancers; but only expressed limitedly on normal cells, which makes STn may serve as a important target in tumor immunotherapy. Based on this, Theratope® (acquired by Merck KGaA), a STn-KLH (keyhole limpet hemocyanin) conjugate, was developed at Biomira Inc., Canada to prevent metastasis of breast and rectal cancers. However, Theratope® was found not to improve time to progression (TTP) or overall survival (OS) when subjected to phase III clinical trial. Improved TTP was achieved only when patients were treated in conjugation with hormone therapy, leading to the prolonged time by 2.5 months (previously 5-8 months) of administration of hormone alone. The dependence on hormone of its anti-tumor activity eclipsed the efficacy of Theratope®. The major obstacle of carbohydrate-based anti-tumor vaccines, as was encountered by Theratope®, is their unsatisfactory performance in inducing immune responses. The conjugation of carbohydrate antigens to immunogenic carrier proteins was generally adopted, but was proved partially by Theratope® relatively ineffective for tumor-associated antigens.

SUMMARY

In one aspect, the present invention provides the solution in the first place to improve the poor immunogenicity of natural carbohydrate-based anti-tumor vaccines by designing and synthesizing novel modified tumor-associated carbohydrate antigens, a type of glycoproteins (-polypeptides) with improved efficacy for anti-tumor therapy.

In a further aspect, the present invention provides the process of preparing the above-mentioned glycoproteins (-polypeptides).

The present invention is to solve the technical problem is achieved by the following technical means:

Firstly, the present invention supplies the sialic acid (α-(2→6))-D-aminopyranose derivatives or salts of the following general formula (1), wherein:

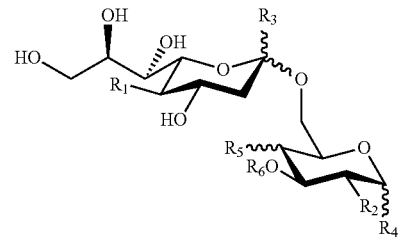

Formula (1)

$R_1$ is optionally acylamino, —$NH_2$, —$N_3$ or —OH; the preferred acylamino groups are —NHC(O)$CH_xCl_y$, —NHC(O)$CH_xF_y$, —NHC(O)$CH_xBr_y$, —NHC(O)H, —NHC(O)$C_aH_{2a+1}$, —NHC(O)$C_aH_{2a}$OH, —NHC(O)$C_bH_{2b-1}$, —NHC(O)$C_bH_{2b-3}$, where x or y is 0, 1, 2 or 3, and the sum of x and y is 3; a is an integer between 1 and 20; b is an integer between 2 and 20;

$R_2$ is optionally acylamno, —$NH_2$, —$N_3$ or —OH; the preferred amido groups are —NHC(O)$CH_pCl_q$, —NHC(O)$CH_pF_q$, —NHC(O)$CH_pBr_q$, —NHC(O)H, —NHC(O)$C_aH_{2a+1}$, —NHC(O)$C_aH_{2a}$OH, —NHC(O)$C_bH_{2b-1}$, —NHC(O)$C_bH_{2b-3}$, where p or q is 0, 1, 2 or 3, and the sum of p and q is 3; a is an integer between 1 and 20; b is an integer between 2 and 20;

$R_3$ is optionally —$CO_2H$, —$CH_2OH$, —$CO_2M$, C(O)NHOH or hydrogen, where M is optionally alkyl, aryl or heteroaryl; the orientation of the $R_3$ is equatorial bond or axial bond;

$R_4$ is optionally substituent group containing alkenyl, alkynyl, azido, aldehyde, protected acetal, maleimido, mercapto group, protected mercapto group, seleno, protected seleno, —NH2 or —ONH2, groups, preferably, R4 is allyl group;

R5 is —OH; the orientation of the R5 is equatorial bond or axial bond;

R6 is optionally hydrogen or β-galactosyl-.

The compounds in Formula 1 are conjugated to proteins or polypeptides to give the corresponding glycoconjugates.

It is understood that compounds in the present invention may be further prepared as salts, which are included in this invention as well.

The salts are preferentially pharmaceutically acceptable and are prepared with non-toxic bases such as sodium bicarbonate, potassium bicarbonate or ammonia, etc. Apart from the preferred ones, other salts are also included in this invention.

The glycoproteins (or -polypeptides) are further prepared as anti-tumor vaccine. Compared with Theratope®, the vaccination results on mice showed 3 to 20-fold increase in antibody titers and improved IgG/IgM ratios by 2 to 14 folds.

The another question the present invention wants to solve is to provides the process of preparing the compound of the following general formula (1).

The another question is to be solved by the following technical means:

A process of preparing N-acyl modified sialic acid (α-(2→6))-D-aminopyranose derivatives or salts of claim 1, which concluding following steps:

Using the sialic acid with 5-naked amino- and/or aminogalactose (aminoglucose) with 2-naked amino- as raw materials, the process is promoted by acylation reaction in the solvents with carboxylic acid anhydrides, carboxylic acids or carboxylic esters in the presence of the reaction promoter.

The preferential raw materials may be allyl 4-O-(5-amino-3,5-dideoxy-α-neuraminopyranosyl)-2-acetylamino-2-deoxy-α-D-galactopyranoside, allyl 4-O-(5-acetylamino-3,5-dideoxy-α-neuraminopyranosyl)-2-amino-2-deoxy-α-D-galactopyranoside or allyl 4-O-(5-amino-3,5-dideoxy-α-neuraminopyranosyl)-2-amino-2-deoxy-α-D-galactopyranoside.

The aliphatic carboxylic anhydride may be chosen, with/without fluoro or chloro substituents. Acetic anhydride, propionic anhydride, n-butyric anhydride, iso-butyric anhydride and caproic anhydride are preferred;

The aliphatic carboxylic acid may be chosen, with/without fluoro or chloro substituents in the aliphatic chain. Mono-, di- or trifluoroaccetic acids and mono- or dichloroacetic acids are preferred;

The aliphatic carboxylic ester may be chosen, with/without fluoro or chloro substituents. Methyl mono-, di- or trifluoroaccetates and methyl dichloroacetates are preferred;

The promoter may be organic or inorganic base;

The solvent may be water or organic solvents.

Still further described below is the technical solution of preparing the glycoconjugate:

(1) The disaccharide in Formula 1 undergoes ozonization to give the corresponding aldehyde; (2) The aldehyde undergoes reductive amination with the carrier protein (or polypeptide) to give the conjugate.

Starting from D-galactosamine (D-glucosamine) and sialic acid, the present invention furnishes the disaccharide derivatives shown in Formula 1 and the corresponding glycoconjugates. In present invention, the acetyl group in natural mono saccharide unit, e.g. sialic acid or amino sugar, is replaced by various modified acyl substituents with novel structures, Some of the synthesized glycoconjugates exhibit improved activities as anti-tumor vaccines. The vaccination results on mice showed that some structurally derivatized TACA-based vaccines possess enhanced immunogenicity with increased antibody titers and raised IgG/IgM ratios. Since STn antigen is expressed abundantly on breast, prostate, pancreas, colorectal and ovarian cancers, the strategy based on antigen modifications with fluoric or other suitable substitutions might find applications in the development of carbohydrate-based and peptide-based vaccines.

BRIEF DESCRIPTION OF THE DRAWINGS

FIG. 2 shows formula of Compounds 1-42 and 61-64.

DETAILED DESCRIPTION OF THE EMBODIMENTS OF THE INVENTION

Figure 1:
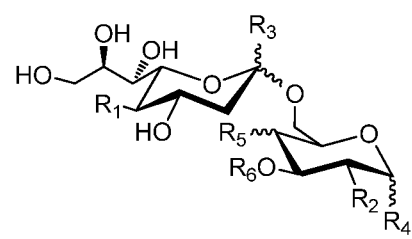
FIG. 1 shows formula of N-acyl modified sialic acid α-(2→6)-D-aminopyranose derivatives.
Figure 3:
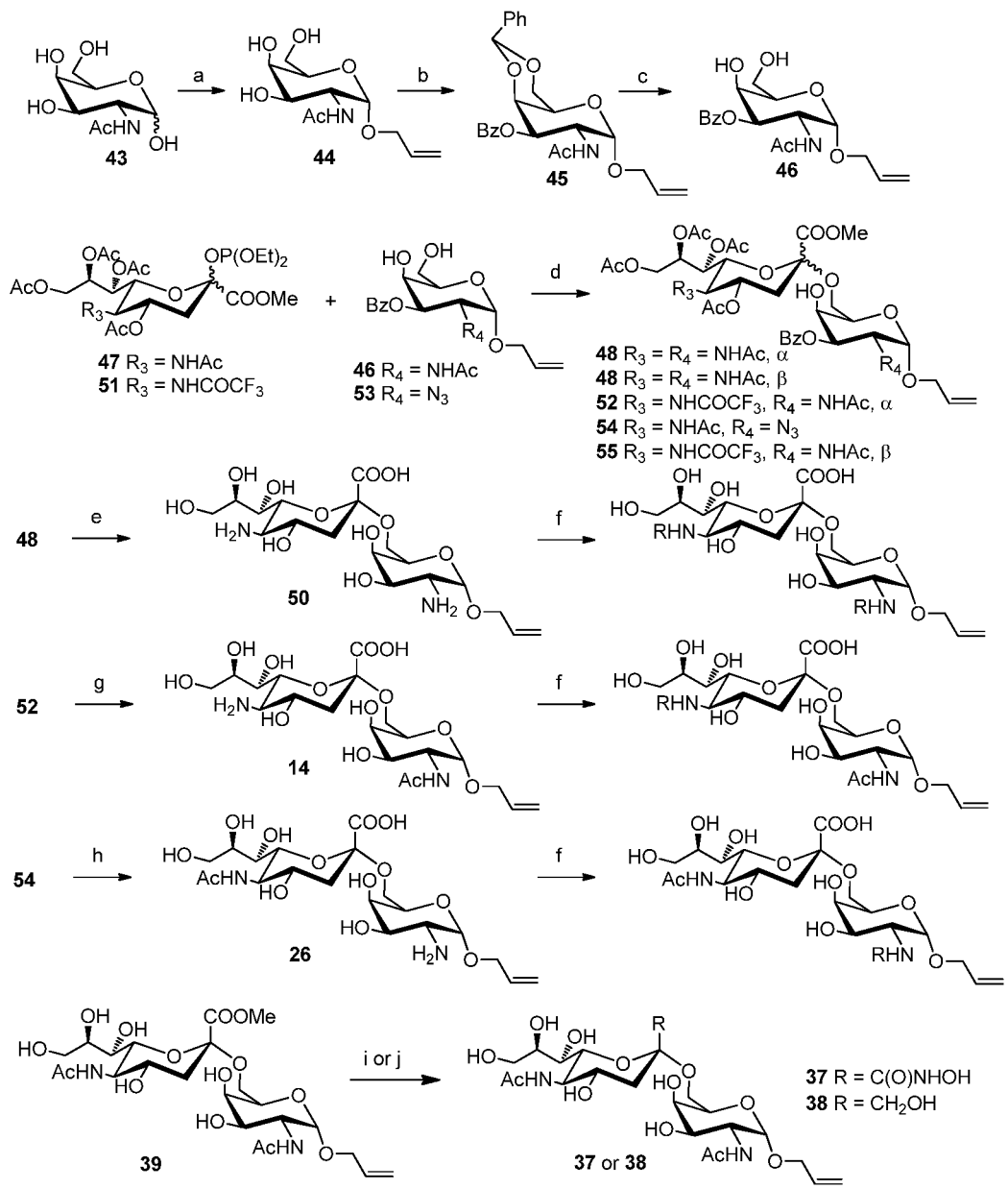
FIG. 3 shows formula of Compounds 43-60 and the synthetic routes of some depicted compounds; and the synthetic route of the antigen. Reagents and conditions: (a-b) see U.S. Pat. No. 6,013,779; (c) strongly acidic cation exchange resin, MeOH, reflux, 97%; (d) TMSOTf, −72° C., THF, for 48 (46+47): 84%, α/β=1/1.2; for 52 (46+51): 81%, α/β=2.6/1; for 54 (47+53): 58%, α only; (e) i. NaOMe/MeOH; ii. 1N NaOH; iii. 2N NaOH, 90° C.; (f) Acylation; (g) NaOMe/MeOH, then 2N NaOH, 86%; (h) i. NaOMe/MeOH, then 1N NaOH; ii. $H_2S$/pyridine/TEA, 67%; (i) for 37, $NH_2OH$, KCN, THF, 50%; (j) for 38, $NaBH_4$, MeOH, 94%.
Figure 4:
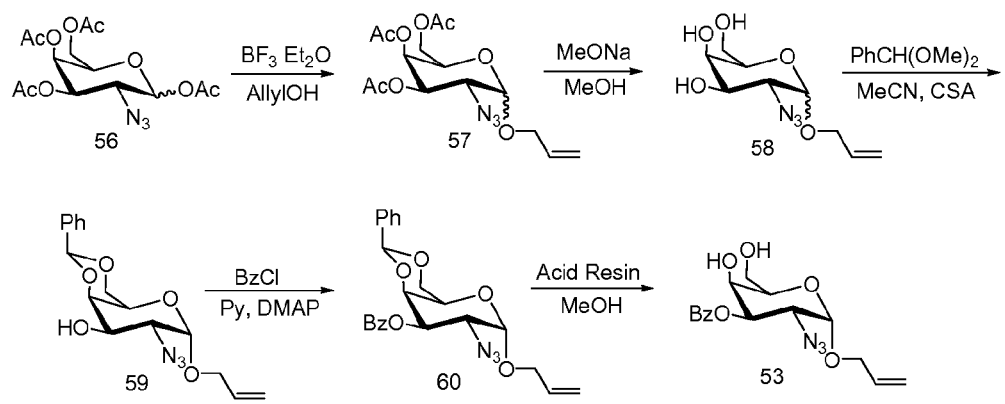
FIG. 4 shows the synthetic routes of Compounds 60 and 53.

Below is the detailed description of the embodiments revealing the advantages of the present invention. The scope of protection of the present invention is not constrained by the representative embodiments described herein. And it should be noted that modificative and alternative technical solutions are included in this invention as well.

Embodiment 1 Synthesis of Compound 2

Compound 48 (100 mg, 0.119 mmol) (For its synthesis, see Embodiment 42.) was dissolved in 10 ml methanol, NaOMe/MeOH (30%, 0.02 g, 0.11 mmol) was added. The mixture was stirred at R.T. for 0.5 h. The reaction mixture was neutralized with 1N HCl/MeOH to pH=3. The mixture was concentrated in vacuum. The residue was purified on a Biogel P-2 column with water as the eluent. Fractions containing the expected product were collected to afford 2 (yield=95%).

$^1$H-NMR (400 MHz, $D_2O$) δ 5.90-5.77 (m, 1H), 5.22 (dd, 1H, $J_1$=1.6 Hz, $J_2$=17.6 Hz), 5.14 (d, 1H, J=10.4 Hz), 4.75 (d, 1H, J=3.6 Hz, anomeric H of GalNAc), 4.15 (dd, 1H, $J_1$=4.0 Hz, $J_2$=13.6 Hz), 4.05 (dd, 1H, $J_1$=4.0 Hz, $J_2$=10.8 Hz), 3.96-3.87 (m, 3H), 3.82-3.74 (m, 5H), 3.60-3.48 (m, 4H), 3.46 (dd, 1H, $J_1$=1.6 Hz, $J_2$=8.8 Hz), 2.59 (dd, 1H, $J_1$=4.4 Hz, $J_2$=12.4 Hz, siaH-3 eq), 1.91 (s, 6H), 1.56 (t, 1H, J=12.4 Hz, siaH-3ax); $^{13}$C-NMR (75 MHz, $D_2O$) 175.59, 175.16, 173.99, 134.221, 118.64, 100.94, 96.79, 73.14, 72.33, 70.09, 69.28, 69.05, 68.80, 68.12, 64.32, 63.17, 52.42, 50.42, 40.83, 22.59, 22.47; HRMS (m/z): $[M+Na]^+$ calcd. for $[C_{22}H_{36}N_2NaO_{14}]^+$, 575.2059. found, 575.2050

Embodiment 2 Synthesis of Compound 3

10 mg Compound 14 [allyl 4-O-(5-amino-3,5-dideoxy-α-D-neuraminopyranosyl)-2-acetylamino-2-deoxy-α-D-galactopyranoside, (10 mg) See Embodiment 13] used as raw material was dissolved in 1 ml methanol. For its synthesis, 2-3 mg NaHCO3 was added. On ice bath, one drop of propionic anhydride (~5 μL) was added. The reaction mixture was stirred for 1 h. Another drop of propionic anhydride was added. After TLC showed the reaction is largely completed. The reaction mixture was then stirred overnight. The temperature was raised to R.T. After TLC showed the reaction is completed, the reaction mixture was neutralized with strong acidic resin and filtered The filtrate was concentrated in vacuum. The residue was purified on a Biogel P-2 column with water as the eluent and was further purified by C18 reverse phase column chromatography with water-water/MeOH as eluent, affording 3 (8-9 mg, yield=75-85%).

$^1$H-NMR (500 MHz, $D_2O$) δ 6.02-5.96 (m, 1H), 5.35 (dq, 1H, J=1.5 Hz, 16.5 Hz), 5.29-5.24 (m, 1H), 4.93 (d, 1H, J=3.5 Hz, anomeric H of GalNAc), 4.21 (ddt, 1H, $J_1$=$J_2$=1.5 Hz, $J_3$=5.5 Hz, $J_4$=13.0 Hz), 4.15 (dd, 1H, $J_1$=3.5 Hz, $J_2$=11.0 Hz), 4.08 (dd, 1H, $J_1$=5.0 Hz, $J_2$=8.0 Hz), 4.04-4.00 (m, 2H), 3.93-3.80 (m, 5H), 3.71-3.61 (m, 4H), 3.56 (dd, 1H, $J_1$=1.5, $J_2$=9.0 Hz), 2.73 (dd, 1H, $J_1$=5.0 Hz, $J_2$=12.5 Hz, siaH-3 eq), 2.28 (q, 2H, J=12.5 Hz), 1.69 (t, 1H, $J_1$=$J_2$=12.5 Hz, siaH-3ax), 1.12 (t, 3H, J=8.0 Hz); $^{13}$C-NMR(75 MHz, $D_2O$) δ179.58, 175.13, 173.98, 134.19, 118.63, 100.91, 96.76, 73.15, 72.31, 70.08, 69.26, 69.03, 68.80, 68.68, 68.09, 64.29, 63.13, 52.27, 50.40, 40.88, 29.80, 22.46, 10.08; HRMS (m/z): [M+Na]$^+$ calcd. for [C$_{23}$H$_{38}$N$_2$NaO$_{14}$]$^+$, 589.2215. found, 589.2223

Embodiment 3 Synthesis of Compound 4

This compound was prepared from Compound 14 and n-butyric anhydride, affording 4 (yield=75-85%). The synthetic procedure was the same as that of Compound 3.

$^1$HNMR (500 MHz, D$_2$O) δ 6.02-5.96 (m, 1H), 5.35 (ddd, 1H, J$_1$=1.5 Hz, J$_2$=3.0 Hz, J$_3$=17.0 Hz), 5.26 (dd, 1H, J$_1$=1.0 Hz, J$_2$=3.0 Hz, J$_3$=10.5 Hz), 4.92 (d, 1H, J=3.5 Hz, anomeric H of GalNAc), 4.22 (ddt, 1H, J$_1$=J$_2$=1.5 Hz, J$_3$=5.5 Hz, J$_4$=13.0 Hz), 4.15 (dd, 1H, J$_1$=3.5 Hz, J$_2$=11.0 Hz), 4.06 (dd, 1H, J$_1$=4.0 Hz, J$_2$=8.0 Hz), 4.04-4.00 (m, 2H), 3.93-3.80 (m, 5H), 3.71-3.61 (m, 4H), 3.56 (dd, 1H, J$_1$=1.5, J$_2$=9.0 Hz), 2.73 (dd, 1H, J$_1$=4.5 Hz, J$_2$=12.5 Hz, siaH-3 eq), 2.26 (t, 2H, J=7.5 Hz), 2.03 (s, 3H), 1.68 (t, 1H, J$_1$=J$_2$=12.5 Hz, siaH-3ax), 1.60 (hexad, 2H, J=7.5 Hz), 0.91 (t, 3H, J=7.5 Hz); $^{13}$C-NMR(75 MHz, D$_2$O) δ 178.88, 175.31, 174.08, 134.40, 118.81, 101.08, 96.98, 73.36, 72.47, 70.26, 69.45, 69.22, 69.10, 68.80, 68.29, 64.46, 63.35, 52.50, 50.59, 41.10, 38.59, 22.66, 19.74, 13.56; HRMS (m/z): [M+Na]$^+$ calcd. for [C$_{24}$H$_{40}$N$_2$NaO$_{14}$]$^+$, 603.2372. found, 603.2379

Embodiment 4 Synthesis of Compound 5

This compound was prepared from Compound 14 and iso-butyric anhydride, affording 5 (yield=75-85%). The synthetic procedure was the same as that of Compound 3.

$^1$H-NMR (500 MHz, D$_2$O) δ 5.95-6.02 (m, 1H), 5.36 (ddd, 1H, J$_1$=1.5 Hz, J$_2$=3.0 Hz, J$_3$=17.5 Hz), 5.26 (m, 1H), 4.92 (d, 1H, J=3.5 Hz, anomeric H of GalNAc), 4.22 (ddt, 1H, J$_1$=J$_2$=1.5 Hz, J$_3$=5.5 Hz, J$_4$=13.0 Hz), 4.15 (dd, 1H, J$_1$=3.5 Hz, J$_2$=11.0 Hz), 4.06 (dd, 1H, J$_1$=4.0 Hz, J$_2$=8.0 Hz), 4.04-3.98 (m, 2H), 3.94-3.78 (m, 5H), 3.74-3.60 (m, 4H), 3.52 (dd, 1H, J$_1$=1.5 Hz, J$_2$=9.0 Hz), 2.75 (dd, 1H, J$_1$=4.5 Hz, J$_2$=12.5 Hz, siaH-3 eq), 2.54 (heptad, 1H, J=7.0 Hz), 2.02 (s, 3H), 1.68 (t, 1H, J$_1$=J$_2$=12.5 Hz, siaH-3ax), 1.12 (d, 3H, J=7.0 Hz), 1.11 (d, 3H, J=7.0 Hz); $^{13}$C-NMR(125 MHz, D$_2$O) δ 182.92, 174.64, 134.01, 119.50, 103.39, 101.79, 100.52, 78.99, 76.22, 75.91, 75.50, 75.14, 73.66, 73.54, 72.50, 71.40, 70.10, 68.95, 68.81, 68.19, 63.26, 61.76, 60.80, 52.19, 40.55, 35.95, 19.69, 19.16; HRMS (m/z): [M+Na]$^+$ calcd. for [C$_{24}$H$_{40}$N$_2$NaO$_{14}$]$^+$, 603.2372. found, 603.2379

Embodiment 5 Synthesis of Compound 6

This compound was prepared from Compound 14 and caproic anhydride, affording 6 (yield=100%). The synthetic procedure was the same as that of Compound 3.

$^1$H-NMR (500 MHz, D$_2$O) δ 6.02-5.96 (m, 1H), 5.35 (dd, 1H, J$_1$=1.5 Hz, J$_1$=3.0 Hz, J$_2$=17.5 Hz), 5.26 (dd, 1H, J$_1$=1.5 Hz, J$_3$=10.5 Hz), 4.92 (d, 1H, J=4.0 Hz, anomeric H of GalNAc), 4.22 (ddd, 1H, J$_1$=1.0 Hz, J$_2$=5.5 Hz, J$_3$=13.0 Hz), 4.15 (dd, 1H, J$_1$=3.5 Hz, J$_2$=11.0 Hz), 4.08-4.00 (m, 3H), 3.93-3.80 (m, 5H), 3.71-3.61 (m, 4H), 3.56 (dd, 1H, J$_1$=1.5, J$_2$=9.0 Hz), 2.73 (dd, 1H, J$_1$=4.5 Hz, J$_2$=12.5 Hz, siaH-3 eq), 2.28 (t, 2H, J=7.5 Hz), 2.03 (s, 3H), 1.68 (t, 1H, J$_1$=J$_2$=12.5 Hz, siaH-3ax), 1.60 (m, 2H), 1.29 (m, 4H), 0.86 (t, 3H, J=7.0 Hz); $^{13}$C-NMR(75 MHz, D$_2$O) δ 179.14, 175.31, 174.12, 134.40, 118.82, 101.11, 96.98, 73.38, 72.51, 70.27, 69.45, 69.22, 69.16, 68.79, 68.29, 64.46, 63.41, 52.49, 50.59, 41.14, 36.62, 31.25, 25.82, 22.66, 22.39, 13.95; HRMS (m/z): [M+Na]$^+$ calcd. for [C$_{26}$H$_{44}$N$_2$NaO$_{14}$]$^+$, 631.2685. found, 631.2684

Embodiment 6 Synthesis of Compound 7

10 mg Compound 14 used as raw material was dissolved in 1 ml methanol, under N$_2$ atmosphere, triethylamine (TEA) (0.4 mL) was added. On ice bath, methyl fluoroacetate (0.2 mL) was added. The temperature was raised to R.T. The reaction mixture can be heated when necessary. When the reaction was near completion (by TLC monitoring), the mixture was concentrated in vacuum. The residue was purified by C18 reverse-phase column chromatography with MeOH/water as eluent and then on a Biogel P-2 column with water as the eluent. The product was still further purified by C18 reverse-phase column chromatography with water-water/MeOH as eluent, affording 7 (yield=75-85%).

$^1$H-NMR (500 MHz, D$_2$O) δ 6.01-5.92 (m, 1H), 5.38-5.30 (m, 1H), 5.28-5.22 (m, 1H), 4.92 (d, 1H, J=4.0 Hz, anomeric H of GalNAc), 4.92 (d, 2H, J=46.0 Hz), 4.23-4.17 (m, 1H), 4.15 (dd, 1H, J$_1$=3.5 Hz, J$_2$=11.0 Hz), 4.06 (dd, 1H, J$_1$=4.0 Hz, J$_2$=8.0 Hz), 4.04-3.80 (m, 9H), 3.71 (dd, 1H, J$_1$=3.5 Hz, J$_2$=10.0 Hz), 3.64 (dd, 1H, J$_1$=6.0 Hz, J$_2$=12.5 Hz), 3.59-3.55 (m, 1H), 2.72 (dd, 1H, J$_1$=4.5 Hz, J$_2$=12.5 Hz, siaH-3 eq), 2.03 (s, 3H), 1.79 (t, 1H, J=12.5 Hz, siaH-3ax); $^{13}$C-NMR(125 MHz, D$_2$O) δ 175.34, 172.48, 172 (d, 1C, J=18.25 Hz), 134.37, 118.80, 100.02, 97.02, 80 (d, 1C, J=180.25 Hz), 73.15, 71.89, 70.20, 69.50, 69.26, 68.94, 68.29, 68.15, 64.56, 63.60, 52.10, 50.56, 40.20, 22.64; HRMS (m/z): [M+Na]$^+$ calcd. for [C$_{22}$H$_{35}$FN$_2$NaO$_{14}$]$^+$, 593.1965. found, 593.1977

Embodiment 7 Synthesis of Compound 8

This compound was prepared from Compound 14 and methyl difluoroacetate, affording 8 (yield=69%). The synthetic procedure was the same as that of Compound 7.

$^1$H-NMR (500 MHz, D$_2$O) δ 6.17 (t, J=54.0 Hz), 6.02-5.92 (m, 1H), 5.35 (dd, 1H, J$_1$=1.5 Hz, J$_1$=3.0 Hz, J$_2$=17.5 Hz), 5.26 (dd, 1H, J$_1$=1.5 Hz, J$_3$=10.5 Hz), 4.92 (d, 1H, J=3.5, anomeric H of GalNAc), 4.22 (dd, 1H, J$_1$=5.5 Hz, J$_2$=13.0 Hz), 4.14 (dd, 1H, J$_1$=3.5 Hz, J$_2$=11.0 Hz), 4.08-3.89 (m, 9H), 3.75 (ddd, 1H, J$_1$=4.5 Hz, J$_2$=9.5 Hz, J$_3$=12.0 Hz), 3.65-3.61 (m, 2H), 3.56 (dd, 1H, J$_1$=1.5, J$_2$=9.0 Hz), 2.74 (dd, 1H, J$_1$=4.5 Hz, J$_2$=12.5 Hz, siaH-3 eq), 2.03 (s, 3H), 1.71 (t, 1H, J=12.5 Hz, siaH-3ax); $^{13}$C-NMR(125 MHz, D$_2$O) δ 175.32, 174.05, 166.30 (m, 1C, CF$_2$HCO—), 134.41, 118.81, 109.03 (t, 1C, J=247.0 Hz, CF$_2$HCO—), 101.13, 96.98, 72.70, 72.60, 70.28, 69.46, 69.24, 68.86, 68.73, 68.28, 64.55, 63.33, 52.62, 50.59, 40.95, 22.65; HRMS (m/z): [M+H]$^+$ calcd. for [C$_{22}$H$_{35}$F$_2$N$_2$O$_{14}$]$^+$, 589.2051. found, 589.2053

Embodiment 8 Synthesis of Compound 9

This compound was prepared from Compound 14 and methyl trifluoroacetate, affording 9 (yield=85%). The synthetic procedure was the same as that of Compound 7.

$^1$H-NMR (500 MHz, D$_2$O) δ 6.02-5.91 (m, 1H), 5.35 (dq, 1H, J=1.5 Hz, 17.5 Hz), 5.26 (dd, 1H, J$_1$=1.5 Hz, J$_3$=10.5 Hz) 4.93 (d, 1H, J=4.0 Hz, anomeric H of GalNAc), 4.20 (ddd, 1H, J$_1$=1.0 Hz, J$_2$=5.5 Hz, J$_3$=13.0 Hz), 4.07 (dd, 1H, J$_1$=4.0 Hz, J$_2$=11.0 Hz), 4.04-3.80 (m, 9H), 3.70 (dd, 1H, J$_1$=4.0 Hz, J$_2$=10.0 Hz), 3.66-3.60 (m, 1H) 3.53 (dd, 1H, J$_1$=1 Hz, J$_2$=9.0 Hz), 2.73 (dd, 1H, J$_1$=4.5 Hz, J$_2$=12.5 Hz, siaH-3 eq), 2.03 (m, 3H), 1.79 (t, 1H, J$_1$=J$_2$=12.5 Hz, siaH-3ax); $^{13}$C-NMR(125 MHz, D$_2$O) δ 175.34, 172.69, 160.19 (q, J=37.2 Hz), 134.39, 118.80, 116.49 (q, J=284.5 Hz), 100.23, 97.02, 72.72, 72.01, 70.21, 69.50, 69.26, 69.00, 64.61, 63.54, 53.07, 50.57, 49.60, 40.36, 22.65; HRMS (m/z): [M+H]$^+$ calcd. for [C$_{22}$H$_{34}$F$_3$N$_2$O$_{14}$]$^+$, 607.1957. found, 607.1936

Embodiment 9 Synthesis of Compound 10

Under N$_2$ atmosphere, Compound 14 (10-15 mg, 0.02-0.03 mmol), HBTU [O-(benzotriazol-1-yl)-tetramethyluronium hexafluorophosphate] (1.3 eq. per amino group) and fluoroacetic acid were dissolved in 2 ml DMF at R.T., DIPEA (N,N-diisopropylethylamine) (13 eq. to Compound 14) was added. After 1-4 h, the reaction was near completion (by TLC monitoring). The mixture was concentrated in vacuum. The residue was purified by C18 reverse-phase column chromatography with MeOH/water as eluent and then on a on a Biogel P-2 column with water as the eluent. The product was still further purified by C18 reverse-phase column chromatography with water-water/MeOH as eluent, affording 10 (yield=56%).

$^1$H-NMR (300 MHz, D$_2$O) δ 5.84-5.65 (m, 1H), 5.35 (d, 1H, J=17.5 Hz), 5.26 (d, 1H, J=10.5 Hz), 4.72 (d, 1H, J=3.6 Hz, anomeric H of GalNAc), 4.04-3.59 (m, 15H), 3.49-3.35 (m, 3H), 2.52 (dd, 1H, J$_1$=4.5 Hz, J$_2$=12.5 Hz, siaH-3 eq), 1.83 (m, 3H), 1.56 (t, 1H, J$_1$=J$_2$=12.0 Hz, siaH-3ax); $^{13}$C-NMR(75 MHz, D$_2$O) δ 175.13, 172.86, 170.99, 134.13, 118.60, 100.08, 96.78, 72.91, 71.86, 70.01, 69.28, 69.04, 68.75, 68.07, 64.37, 63.32, 52.72, 50.35, 42.82, 40.26, 22.42; HRMS (m/z): [M+Na]$^+$ calcd. for C$_{22}$H$_{35}$ClN$_2$NaO$_{14}$, 609.1669. found, 609.1675

Embodiment 10 Synthesis of Compound 11

This compound was prepared from Compound 14 and methyl dichloroacetate, affording 11 (yield=46%). The synthetic procedure was the same as that of Compound 7.

$^1$H-NMR (300 MHz, D$_2$O) δ 6.14 (s, 1H), 5.87-5.72 (m, 1H), 5.17 (d, 1H, J=17.1 Hz), 5.08 (d, 1H, J=10.2 Hz), 4.77 (d, 1H, J=3.6 Hz, anomeric H of GalNAc), 4.06-3.56 (m, 18H), 2.56 (dd, 1H, J$_1$=4.0 Hz, J$_2$=12.6 Hz, siaH-3 eq), 1.86 (s, 3H), 1.62 (t, 1H, J$_1$=J$_2$=12.0 Hz, siaH-3ax); $^{13}$C-NMR (125 MHz, D$_2$O) δ 175.34, 172.45, 168.22, 134.39, 118.81, 100.03, 97.03, 73.09, 71.95, 70.20, 69.51, 69.27, 69.15, 68.30, 68.00, 66.93, 64.58, 63.61, 53.25, 50.56, 40.32, 22.65; HRMS (m/z): [M+Na]$^+$ calcd. for [C$_{22}$H$_{34}$Cl$_2$N$_2$NaO$_{14}$]$^+$, 643.1279. found, 643.1304

Embodiment 11 Synthesis of Compound 12

This compound was prepared from Compound 14 and methyl trichloroacetate, affording 12 (yield=64%). The synthetic procedure was the same as that of Compound 7.

$^1$H-NMR (500 MHz, D$_2$O) δ 6.02-5.92 (m, 1H), 5.35 (dd, 1H, J$_1$=1.5 Hz, J$_2$=17.0 Hz), 5.26 (d, 1H, J=10.5 Hz), 4.93 (d, 1H, J=3.5 Hz, anomeric H of GalNAc), 4.21 (dd, 1H, J$_1$=5.5 Hz, J$_2$=12.5 Hz), 4.15 (dd, 1H, J$_1$=4.0 Hz, J$_2$=12.5 Hz), 4.09-3.83 (m, 9H), 3.67-3.57 (m, 3H) 3.53 (dd, 1H, J$_1$=1 Hz, J$_2$=9.0 Hz), 2.75 (dd, 1H, J$_1$=4.5 Hz, J$_2$=12.5 Hz, siaH-3 eq), 2.03 (s, 3H), 1.74 (t, 1H, J$_1$=J$_2$=12.5 Hz, siaH-3ax); $^{13}$C-NMR(125 MHz, D$_2$O) δ 175.34, 173.76, 165.54, 134.42, 118.82, 100.90, 97.00, 72.67, 72.59, 70.28, 69.48, 69.25, 69.22, 68.29, 64.58, 63.38, 54.58, 50.59, 41.13, 22.67; HRMS (m/z): [M+Na]$^+$ calcd. for [C$_{22}$H$_{33}$Cl$_3$N$_2$NaO$_{14}$]$^+$, 677.0890. found, 677.0902

Embodiment 12 Synthesis of Compound 13

Compound 14 (15.0 mg, 0.029 mmol) was dissolved in 2.0 ml methanol, CuSO$_4$ (0.5 mg, 0.003 mmol) was added. TfN$_3$/pyridine (8.0 mL, 0.56 mmol See *Tetrahedron Lett.* 2005, 46, 8993-8995) was then added to the mixture. The reaction went to completion after 1 h (by TLC monitoring). The mixture was concentrated in vacuum. The residue was purified by C18 reverse-phase column chromatography with MeOH/water as eluent and then on a Biogel P-2 column with water as the eluent. The product was still further purified by C18 reverse-phase column chromatography with water-water/MeOH as eluent, affording 13 (yield=96%).

$^1$H-NMR (500 MHz, D$_2$O) δ 5.93-6.00 (m, 1H), 5.35 (ddd, 1H, J$_1$=1.5 Hz, J$_2$=3.0 Hz, J$_3$=17.5 Hz), 5.26 (ddd, 1H, J$_1$=1.0 Hz, J$_2$=2.5 Hz, J$_3$=10.5 Hz), 4.92 (d, 1H, J=3.5 Hz, anomeric H of GalNAc), 4.21 (ddd, 1H, J$_1$=1.0 Hz, J$_2$=5.5 Hz, J$_3$=13.0 Hz), 4.14 (dd, 1H, J$_1$=3.5 Hz, J$_2$=11.0 Hz), 4.08-3.99 (m, 3H), 3.93-3.88 (m, 4H), 3.80 (dd, 1H, J$_1$=2.0 Hz, J$_2$=9.0 Hz), 3.72-3.64 (m, 2H), 3.64-3.58 (m, 2H), 3.47 (dd, 1H, J$_1$=J$_2$=10.0 Hz), 2.72 (dd, 1H, J$_1$=5.0 Hz, J$_2$=13.0 Hz, siaH-3 eq), 2.03 (s, 3H), 1.68 (t, 1H, J$_1$=J$_2$=12.5 Hz, siaH-3ax); $^{13}$C-NMR (125 MHz, D$_2$O) δ 175.33, 173.99, 134.42, 118.80, 101.11, 96.98, 73.27, 72.67, 70.28, 70.13, 69.46, 69.29, 69.25, 68.28, 64.58, 63.49, 63.33, 50.60, 40.80, 22.66; HRMS (m/z): [M+Na]$^+$ calcd. for [C$_{20}$H$_{32}$N$_4$NaO$_{13}$]$^+$, 559.1858. found, 559.1847

Embodiment 13 Synthesis of Compound 14

Compound 52 (For its synthesis, see Embodiment 44) (380 mg, 0.426 mmol) was dissolved in 20 ml methanol, NaOMe/MeOH (30%, 0.02 g, 011 mmol) was added. The mixture was stirred at R.T. for 1 h. The mixture was concentrated in vacuum. The solution of NaOH in water (2N, 10 mL) was added. The mixture was stirred at R.T. for 10 h. The reaction mixture was neutralized with 1N HCl/MeOH to pH=3. The mixture was concentrated in vacuum. The residue was purified on a Biogel P-2 column with water as the eluent. Fractions containing the expected product were collected to afford 2 (yield=86%). The crude product may also be directly used in the next step.

$^1$H-NMR (500 MHz, D$_2$O) δ 5.97 (m, 1H), 5.35 (ddd, 1H, J$_1$=1.5 Hz, J$_2$=3.0 Hz, J$_3$=17.5 Hz), 5.26 (ddd, 1H, J$_1$=1.5 Hz, J$_2$=3.0 Hz, J$_3$=10.5 Hz), 4.93 (d, 1H, J=4.0 Hz, anomeric H of GalNAc), 4.20 (ddd, 1H, J$_1$=1.0 Hz, J$_2$=5.5 Hz, J$_3$=13.0 Hz), 4.14 (dd, 1H, J$_1$=3.5 Hz, J$_2$=12.0 Hz), 4.07 (dd, 1H, J$_1$=4.0 Hz, J$_2$=11.0 Hz), 4.04-3.89 (m, 7H), 3.80-3.71 (m, 3H), 3.62 (dd, 1H, J$_1$=4.0 Hz, J$_2$=10.5 Hz), 3.22 (t, 1H, J$_1$=J$_2$=10.0 Hz), 2.77 (dd, 1H, J$_1$=4.5 Hz, J$_2$=12.5 Hz, siaH-3 eq), 2.03 (m, 3H), 1.71 (t, 1H, J$_1$=J$_2$=12.5 Hz, siaH-3ax); $^{13}$C-NMR (75 MHz, D$_2$O) δ 175.06, 173.57, 134.14, 118.57, 100.80, 96.71, 72.25, 72.15, 70.04, 69.20, 69.04, 68.37, 67.98, 67.72, 64.51, 62.77, 52.79, 50.34, 40.82, 22.45; HRMS (m/z): [M+Na]$^+$ calcd. for [C$_{20}$H$_{34}$N$_2$NaO$_{13}$]$^+$, 533.1953. found, 533.1953

Embodiment 14 Synthesis of Compound 15

This compound was prepared from Compound 14 and bromoacetic acid, affording 15 (yield=37%). The synthetic procedure was the same as that of Compound 10.

$^1$H-NMR (500 MHz, D$_2$O) δ 6.02-5.92 (m, 1H), 5.35 (dq, 1H, J=1.5 Hz, 17.5 Hz), 5.26 (dq, 1H, J=1.5 Hz, 10.5 Hz), 4.92 (d, 1H, J=4.0 Hz, anomeric H of GalNAc), 4.22 (ddt, 1H, J$_1$=J$_2$=1.5 Hz, J$_3$=4.0 Hz, J$_3$=13.0 Hz), 4.15 (dd, 1H, J$_1$=3.5 Hz, J$_2$=6.0 Hz), 4.07 (dd, 1H, J$_1$=4.5 Hz, J$_2$=8.0 Hz), 4.05-4.00 (m, 2H), 3.96-3.85 (m, 7H), 3.80 (dd, 1H, J$_1$=1.5 Hz, J$_2$=10.5 Hz), 3.71 (ddd, 1H, J$_1$=4.5 Hz, J$_2$=9.5 Hz, J$_3$=12.0 Hz), 3.66-3.59 (m, 3H), 2.73 (dd, 1H, J$_1$=4.5 Hz, J$_2$=12.5 Hz, siaH-3 eq), 2.04 (s, 3H), 1.69 (dd, 1H, J$_1$=J$_2$=12.5 Hz, siaH-3ax); $^{13}$C-NMR (125 MHz, D$_2$O) δ 175.34, 174.12, 171.51, 134.42, 118.82, 101.15, 96.99, 73.13, 72.63, 70.29, 69.47, 69.24, 69.02, 68.30, 64.52, 63.38, 53.03, 50.61, 41.04, 28.73, 22.67; HRMS (m/z): [M+H]$^+$ calcd. for [C$_{22}$H$_{36}$BrN$_2$O$_{14}$]$^+$, 631.1344. found, 631.1324

Embodiment 15 Synthesis of Compound 16

This compound was prepared from Compound 26 [allyl 4-O-(5-acetylamino-3,5-dideoxy-α-D-neuraminopyranosyl)-2-amino-2-deoxy-α-D-galactopyranoside. See Embodiment 25] and propionic anhydride, affording 16 (yield=56%). The synthetic procedure was the same as that of Compound 3.

$^1$H-NMR (500 MHz, D$_2$O) δ 6.01-5.91 (m, 1H), 5.35 (dd, 1H, J$_1$=1.5 Hz, J$_2$=17.5 Hz), 5.25 (d, 1H, J=10.5 Hz), 4.92 (d, J=3.5 Hz, anomeric H of GalN), 4.21 (dd, 1H, J$_1$=5.0 Hz, J$_2$=12.5 Hz), 4.15 (dd, 1H, J$_1$=3.5 Hz, J$_2$=11.5 Hz), 4.07 (dd, 1H, J$_1$=4.5 Hz, J$_2$=7.5 Hz), 4.04-3.99 (m, 2H), 3.94-3.81 (m, 5H), 3.73-3.62 (m, 4H), 3.57 (dd, 1H, J$_1$=1.5 Hz, J$_2$=9.0 Hz), 2.72 (dd, 1H, J$_1$=4.5 Hz, J$_2$=12.5 Hz, siaH-3 eq), 2.03 (t, 1H, J$_1$=J$_2$=8.0 Hz), 2.29 (q, 2H, J=7.5 Hz), 2.03 (s, 3H), 1.70 (t, 1H, J$_1$=J$_2$=12.0 Hz, siaH-3ax), 1.11 (t, 3H, J$_1$=J$_2$=7.5 Hz);

$^{13}$C-NMR (125 MHz, D$_2$O) δ 179.33, 175.76, 174.14, 134.36, 118.89, 101.13, 96.96, 73.33, 72.50, 70.28, 69.48, 69.25, 68.98, 68.22, 64.49, 63.36, 52.59, 50.49, 41.00, 29.84, 22.76, 10.29; HRMS (m/z): [M+Na]$^+$ calcd. for [C$_{23}$H$_{38}$N$_2$NaO$_{14}$]$^+$, 589.2215. found, 589.2225

Embodiment 16 Synthesis of Compound 17

This compound was prepared from Compound 26 and n-butyric anhydride, affording 17 (yield=53%). The synthetic procedure was the same as that of Compound 3.

$^1$H-NMR (500 MHz, D$_2$O) δ 6.00-5.90 (m, 1H), 5.35 (dd, 1H, J$_1$=1.5 Hz, J$_2$=17.5 Hz), 5.26 (d, 1H, J$_1$=1.0 Hz, J$_2$=10.5 Hz), 4.92 (d, 1H, J=3.5 Hz, anomeric H of GalN), 4.20 (dd, 1H, J$_1$=5.5 Hz, J$_2$=13.0 Hz), 4.14 (dd, 1H, J$_1$=3.5 Hz, J$_2$=11.5 Hz), 4.06 (dd, 1H, J$_1$=4.5 Hz, J$_2$=7.5 Hz), 4.03-3.99 (m, 2H), 3.94-3.80 (m, 5H), 3.71-3.61 (m, 4H), 3.78 (dd, 1H, J$_1$=1.5 Hz, J$_2$=9.0 Hz), 2.73 (dd, 1H, J$_1$=5.0, J$_2$=12.5 Hz, siaH-3 eq), 2.28 (t, 2H, J=7.0 Hz), 2.03 (s, 1H), 1.68 (t, 1H, J$_1$=J$_2$=12.5 Hz, siaH-3ax), 1.65-1.56 (m, 2H), 0.93 (t, 3H, J=7.5 Hz); $^{13}$C-NMR(125 MHz, D$_2$O) δ 178.26, 175.59, 173.89, 134.14, 118.82, 100.88, 96.8473.16, 72.29, 70.10, 69.36, 69.10, 68.78, 67.96, 64.33, 63.19, 52.41, 50.36, 40.79, 38.19, 22.59, 19.60, 13.26; HRMS (m/z): [M+Na]$^+$ calcd. for [C$_{24}$H$_{40}$N$_2$NaO$_{14}$]$^+$, 603.2372. found, 603.2374

Embodiment 17 Synthesis of Compound 18

This compound was prepared from Compound 26 and iso-butyric anhydride, affording 18 (yield=76%). The synthetic procedure was the same as that of Compound 3.

$^1$H-NMR (500 MHz, D$_2$O) δ 6.00-5.90 (m, 1H), 5.35 (dd, 1H, J$_1$=1.5 Hz, J$_2$=17.0 Hz), 5.26 (d, 1H, J$_1$=10.0 Hz), 4.92 (d, 1H, J=4.0 Hz, anomeric H of GalN), 4.20 (dd, 1H, J$_1$=5.0 Hz, J$_2$=13.0 Hz), 4.14 (dd, 1H, J$_1$=4.0 Hz, J$_2$=11.5 Hz), 4.06 (dd, 1H, J$_1$=4.5 Hz, J$_2$=8.0 Hz), 4.03-3.99 (m, 2H), 3.94-3.80 (m, 5H), 3.71-3.61 (m, 4H), 3.78 (dd, 1H, J$_1$=1.5 Hz, J$_2$=8.5 Hz), 2.73 (dd, 1H, J$_1$=4.5, J$_2$=12.5 Hz, siaH-3 eq), 2.56 (septenary, 1H, J=7.0 Hz), 2.03 (s, 3H), 1.83 (t, 1H, J$_1$=J$_2$=12.5 Hz, siaH-3ax), 1.10 (d, 3H, J=7.0 Hz), 1.09 (d, 3H, J=7.0 Hz); $^{13}$C-NMR(125 MHz, D$_2$O) δ 182.45, 175.76, 174.12, 134.31, 119.00, 101.11, 96.91, 73.32, 72.49, 70.29, 69.50, 69.28, 68.97, 6810, 64.49, 63.36, 52.58, 50.43, 40.98, 35.71, 22.76, 19.61, 19.19; HRMS (m/z): [M+Na]$^+$ calcd. for [C$_{24}$H$_{40}$N$_2$NaO$_{14}$]$^+$, 603.2372. found, 603.2384

Embodiment 18 Synthesis of Compound 19

This compound was prepared from Compound 26 and caproic anhydride, affording 19 (yield=87%). The synthetic procedure was the same as that of Compound 3.

$^1$H-NMR (500 MHz, D$_2$O) δ 6.01-5.93 (m, 1H), 5.35 (dd, 1H, J$_1$=1.5 Hz, J$_2$=17.5 Hz), 5.26 (d, 1H, J$_1$=1.0 Hz, J$_2$=10.5 Hz), 4.92 (d, 1H, J=3.5 Hz, anomeric H of GalN), 4.22 (dd, 1H, J$_1$=5.0 Hz, J$_2$=13.0 Hz), 4.15 (dd, 1H, J$_1$=4.0 Hz, J$_2$=11.0 Hz), 4.07 (dd, 1H, J$_1$=4.0 Hz, J$_2$=8.0 Hz), 4.08-4.00 (m, 2H), 3.93-3.80 (m, 5H), 3.71-3.61 (m, 4H), 3.56 (dd, 1H, J$_1$=1.5, J$_2$=9.0 Hz), 2.73 (dd, 1H, J$_1$=4.5 Hz, J$_2$=12.5 Hz, siaH-3 eq), 2.28 (m, 2H), 2.03 (s, 3H), 1.68 (t, 1H, J=12.5 Hz, siaH-3ax), 1.60 (m, 2H), 1.29 (m, 4H), 0.86 (t, 3H, J=7.0 Hz); $^{13}$C-NMR(125 MHz, D$_2$O) δ 178.62, 175.76, 174.12, 134.32, 118.98, 101.13, 97.02, 73.33, 72.50, 70.28, 69.54, 69.26, 68.98, 68.13, 64.48, 63.36, 52.59, 50.52, 40.99, 36.44, 31.14, 25.83, 22.76, 22.41, 13.95; HRMS (m/z): [M+Na]$^+$ calcd. for [C$_{26}$H$_{44}$N$_2$NaO$_{14}$]$^+$, 631.2685. found, 631.2678

Embodiment 19 Synthesis of Compound 20

This compound was prepared from Compound 26 and methyl fluoroacetate, affording 20 (yield=77%). The synthetic procedure was the same as that of Compound 7.

$^1$H-NMR (500 MHz, D$_2$O) δ 6.02-5.92 (m, 1H), 5.35 (dd, 1H, J$_1$=1.0 Hz, J$_2$=17.0 Hz), 5.26 (d, 1H, J=10.5 Hz), 4.97 (d, J=4.0 Hz, anomeric H of GalN), 4.97&4.88 (d, 2H, J$_{F,H}$=46.5 Hz), 4.26 (dd, 1H, J$_1$=4.0 Hz, J$_2$=11.0 Hz), 4.22 (dd, 1H, J$_1$=5.0 Hz, J$_2$=13.0 Hz), 4.08 (dd, 1H, J$_1$=4.5 Hz, J$_2$=8.0 Hz), 4.05-3.99 (m, 3H), 3.94-3.81 (m, 4H), 3.71-3.62 (m, 4H), 3.58 (dd, 1H, J$_1$=1.5 Hz, J$_2$=9.0 Hz), 2.72 (dd, 1H, J$_1$=4.5 Hz, J$_2$=12.5 Hz, siaH-3 eq), 2.03 (s, 3H), 1.68 (t, 1H J$_1$=J$_2$=12.5 Hz, siaH-3ax); $^{13}$C-NMR(125 MHz, D$_2$O) δ 175.77, 174.14, 171.89, 171.74, 134.35, 118.94, 101.13, 96.88, 81.18, 79.74, 73.33, 72.50, 70.33, 69.50, 69.22, 69.00, 68.10, 64.45, 63.36, 52.59, 50.28, 41.00, 22.76; HRMS (m/z): [M+Na]$^+$ calcd. for [C$_{22}$H$_{35}$FN$_2$NaO$_{14}$]$^+$, 593.1965. found, 593.1975

Embodiment 20 Synthesis of Compound 21

This compound was prepared from Compound 26 and methyl difluoroacetate, affording 21 (yield=78%). The synthetic procedure was the same as that of Compound 7.

$^1$H-NMR (500 MHz, D$_2$O) δ 6.19 (t, 1H, J$_{F,H}$=53.6 Hz), 6.01-5.91 (m, 1H), 5.34 (dq, 1H, J=1.5 Hz, 17.5 Hz), 5.25 (dq, 1H, J=1.5 Hz, 10.5 Hz), 4.99 (d, J=4.0 Hz, anomeric H of GalN), 4.26-4.19 (m, 2H), 4.10 (dd, 1H, J$_1$=4.0 Hz, J$_2$=8.0 Hz), 4.06-3.99 (m, 3H), 3.99-3.93 (m, 1H), 3.90-3.84 (m, 3H), 3.80-3.69 (m, 3H), 3.65 (dd, 1H, J$_1$=6.5 Hz, J$_2$=12.5 Hz), 3.57 (dd, 1H, J$_1$=1.5 Hz, J$_2$=8.5 Hz), 2.71 (dd, 1H, J$_1$=5.0 Hz, J$_2$=13.0 Hz, siaH-3 eq), 2.03 (s, 3H), 1.76 (t, J$_1$=J$_2$=12.0 Hz, siaH-3ax); $^{13}$C-NMR(125 MHz, D$_2$O) δ 175.73, 172.88, 166.05 (t, 1C), 134.29, 118.97, 118.79, 108.88 (t, 1C, J$_{F-C}$=246.1 Hz), 100.27, 96.61, 73.50, 71.99, 70.28, 69.55, 69.20, 69.02, 68.50, 67.93, 64.46, 63.57, 52.51, 50.90, 50.82, 40.36, 22.79; HRMS (m/z): [M+Na]$^+$ calcd. for [C$_{22}$H$_{34}$F$_2$N$_2$NaO$_{14}$]$^+$, 611.1870. found, 611.1861

Embodiment 21 Synthesis of Compound 22

This compound was prepared from Compound 26 and methyl trifluoroacetate, affording 22 (yield=76%). The synthetic procedure was the same as that of Compound 7.

$^1$H-NMR (500 MHz, D$_2$O) δ 5.92-5.82 (m, 1H), 5.35 (d, 1H, J=17.0 Hz), 5.26 (d, 1H, J=10.5 Hz), 4.92 (d, 1H, J=3.5 Hz, anomeric H of GalN), 4.20-4.11 (m, 2H), 4.01 (dd, 1H, J$_1$=4.5 Hz, J$_2$=7.0 Hz), 4.00-3.91 (m, 3H), 3.86-3.72 (m, 5H), 3.65-3.51 (m, 4H), 3.50 (d, 1H, J=9.0 Hz), 2.65 (dd, 1H, J$_1$=4.5 Hz, J$_2$=12.5 Hz, siaH-3 eq), 1.95 (s, 3H), 1.60 (t, 1H, J$_1$=J$_2$=12.5 Hz, siaH-3ax); $^{13}$C-NMR(125 MHz, D$_2$O) δ 175.07, 173.34, 159.38 (q, J$_{F-C}$=37.5 Hz), 133.59, 118.30, 116 (q, J$_{F-C}$=284.1 Hz), 100.40, 95.65, 72.63, 71.77, 69.62, 68.82 68.46, 68.29, 68.23, 66.97, 63.69, 62.68, 51.89, 50.75, 40.25 HRMS (m/z): [M+Na]$^+$ calcd. for [C$_{22}$H$_{33}$F$_3$N$_2$NaO$_{14}$]$^+$, 629.1776. found, 629.1787

Embodiment 22 Synthesis of Compound 23

This compound was prepared from Compound 26 and chloroacetic acid, affording 23 (yield=54%). The synthetic procedure was the same as that of Compound 10.

$^1$H-NMR (500 MHz, D$_2$O) δ 6.01-5.92 (m, 1H), 5.35 (dq, 1H, J=1.5 Hz, 17.5 Hz), 5.27 (dd, 1H, J$_1$=1.5 Hz, J$_2$=10.5 Hz), 4.95 (d, 1H, J=4.0 Hz, anomeric H of GalN), 4.24-4.18 (m, 3H), 4.16 (d, 1H, J=0.5 Hz), 4.08 (dd, 1H, J$_1$=5.0 Hz, J$_2$=8.0 Hz), 4.06-4.00 (m, 2H), 3.96 (dd, 1H, J$_1$=3.0 Hz, J$_2$=11.0 Hz), 3.92-3.80 (m, 4H), 3.70 (dd, 1H, J$_1$=2.0 Hz, J$_2$=8.5 Hz), 3.68-3.60 (m, 3H), 3.58 (dd, 1H, J$_1$=2.0 Hz, J$_2$=9.0 Hz), 2.72 (dd, 1H, J$_1$=4.5 Hz, J$_2$=12.5 Hz, siaH-3 eq), 1.83 (s, 3H), 1.56 (t, 1H, J=12.0 Hz, siaH-3ax); $^{13}$C-NMR (125 MHz, D$_2$O) δ 175.77, 174.12, 170.85, 134.33, 118.98, 101.12, 96.75, 73.33, 72.50, 70.34, 69.53, 69.21, 68.99, 68.21, 64.46, 63.36, 52.59, 51.11, 42.97, 40.99, 22.76; HRMS (m/z): [M+NH$_4$]$^+$ calcd. for [C$_{22}$H$_{39}$ClN$_3$O$_{14}$]$^+$, 604.2115. found, 604.2112

Embodiment 23 Synthesis of Compound 24

This compound was prepared from Compound 26 and methyl dichloroacetate, affording 24 (yield=54%). The synthetic procedure was the same as that of Compound 7.

$^1$H-NMR (500 MHz, D$_2$O) δ 6.35 (s, 1H), 6.01-5.92 (m, 1H), 5.35 (dd, 1H, J$_1$=1.5 Hz, J$_2$=17.5 Hz), 5.26 (d, 1H, J=10.5 Hz), 4.92 (d, 1H, J=4.0 Hz, anomeric H of GalN), 4.22 (dd, 1H, J$_1$=5.5 Hz, J$_2$=13.0 Hz), 4.17 (dd, 1H, J$_1$=3.5 Hz, J$_2$=6.0 Hz), 4.08 (dd, 1H, J$_1$=4.5 Hz, J$_2$=8.0 Hz), 4.05-4.00 (m, 2H), 3.98 (dd, 1H, J$_1$=3.0 Hz, J$_2$=11.0 Hz), 3.94-3.80 (m, 4H), 3.71 (dd, 1H, J$_1$=2.0 Hz, J$_2$=10.5 Hz), 3.69-3.62 (m, 3H), 3.58 (dd, 1H, J$_1$=1.5 Hz, J$_2$=8.5 Hz), 2.73 (dd, 1H, J$_1$=5.5 Hz, J$_2$=12.5 Hz, siaH-3 eq), 2.03 (s, 3H), 1.69 (t, 1H, J=12.0 Hz, siaH-3ax); $^{13}$C-NMR(125 MHz, D$_2$O) δ 175.77, 174.06, 168.02, 134.28, 119.15, 101.09, 96.40, 73.34, 72.48, 70.36, 69.60, 69.24, 69.00, 68.96, 68.03, 66.77, 64.44, 63.38, 52.59, 51.64, 40.96, 22.77; HRMS (m/z): [M+H]$^+$ calcd. for [C$_{22}$H$_{35}$Cl$_2$N$_2$O$_{14}$]$^+$, 621.1460. found, 621.1477

Embodiment 24 Synthesis of Compound 25

Compound 54 (For its synthesis, see Embodiment 45) (145 mg, 0.176 mmol) was dissolved in 8.0 ml methanol, NaOMe/MeOH (30%, 0.02 g, 0.11 mmol) was added. The mixture was stirred at R.T. for 2 h. The mixture was concentrated in vacuum. The solution of NaOH in water (1N, 3 mL) was added. The mixture was stirred at R.T. for 24 h. The reaction mixture was neutralized with 1N HCl/MeOH to pH=3. The mixture was concentrated in vacuum. The residue was purified on a Biogel P-2 column with water as the eluent. Fractions containing the expected product were collected to afford 25 (yield=100%).

$^1$H-NMR (500 MHz, D$_2$O) δ 6.02-5.94 (m, 1H), 5.35 (ddd, 1H, J$_1$=1.5 Hz, J$_2$=3.0 Hz, J$_3$=17.5 Hz), 5.26 (ddd, 1H, J$_1$=1.0 Hz, J$_2$=2.5 Hz, J$_3$=10.5 Hz), 4.92 (d, 1H, J=3.5 Hz, anomeric H of GalN$_3$), 4.21 (ddd, 1H, J$_1$=1.0 Hz, J$_2$=5.5 Hz, J$_3$=13.0 Hz), 4.14 (dd, 1H, J$_1$=3.5 Hz, J$_2$=11.0 Hz), 4.08-3.99 (m, 3H), 3.93-3.88 (m, 4H), 3.80 (dd, 1H, J$_1$=2.0 Hz, J$_2$=9.0 Hz), 3.72-3.64 (m, 2H), 3.64-3.58 (m, 2H), 3.47 (dd, 1H, J$_1$=J$_2$=10.0 Hz), 2.72 (dd, 1H, J$_1$=5.0 Hz, J$_2$=13.0 Hz, siaH-3 eq), 2.03 (s, 3H), 1.68 (t, 1H, J=12.5 Hz, siaH-3ax); $^{13}$C-NMR (125 MHz, D$_2$O) δ 175.33, 173.99, 134.42, 118.80, 101.11, 96.98, 73.27, 72.67, 70.28, 70.13, 69.46, 69.29, 69.25, 68.28, 64.58, 63.49, 63.33, 50.60, 40.80, 22.66; HRMS (m/z): [M+Na]$^+$ calcd. for [C$_{20}$H$_{32}$N$_4$NaO$_{13}$]$^+$, 559.1858. found, 559.1851

Embodiment 25 Synthesis of Compound 26

Compound 25 (94 mg, 0.176 mmol. For its synthesis, see Embodiment 24) was dissolved in solution comprising of 15 ml pyridine, 10 ml TEA and 5 ml water, H$_2$S was introduced. The reaction mixture was stirred for 10 h. The mixture was concentrated in vacuum. The residue was purified on a Biogel P-2 column with water as the eluent. Fractions containing the expected product were collected to afford 26 (yield=67%).

$^1$H-NMR (500 MHz, D$_2$O) δ 6.02-5.97 (m, 1H), 5.38 (d, 1H, J=17.0 Hz), 5.28 (d, J=10.0 Hz), 5.17 (d, 1H, J=3.5 Hz, anomeric H of GalNH$_2$), 4.28 (dd, 1H, J$_1$=5.5 Hz, J$_2$=12.5 Hz), 4.14-4.00 (m, 4H), 3.93-3.80 (m, 4H), 3.71-3.56 (m, 5H), 3.48 (dd, 1H, J$_1$=3.5 Hz, J$_2$=11.0 Hz), 2.73 (dd, 1H, J$_1$=4.5 Hz, J$_2$=12.5 Hz, siaH-3 eq), 2.03 (s, 3H), 1.68 (t, 1H, J=12.0 Hz, siaH-3ax); $^{13}$C-NMR (125 MHz, D$_2$O) δ 175.61, 173.94, 133.74, 119.33, 100.95, 94.97, 73.16, 72.34, 70.29, 69.56, 68.74, 68.56, 67.10, 64.04, 63.16, 52.40, 51.36, 40.78, 22.58; HRMS (m/z): [M+Na]$^+$ calcd. for [C$_{20}$H$_{34}$N$_2$NaO$_{13}$]$^+$, 533.1953. found, 533.1957

Embodiment 26 Synthesis of Compound 27

This compound was prepared from Compound 50 [allyl 4-O-(5-amino-3,5-dideoxy-α-D-neuraminopyranosyl)-2-amino-2-deoxy-α-D-galactopyranoside. For its synthesis, see embodiment 43] and propionic anhydride, affording 27 (yield=55%). The synthetic procedure was the same as that of Compound 3.

$^1$H-NMR (500 MHz, D$_2$O) δ 6.01-5.92 (m, 1H), 5.35 (dq, 1H, J=1.5 Hz, 17.5 Hz), 5.26 (dd, 1H, J$_1$=1.5 Hz, J$_3$=10.5 Hz), 4.91 (d, 1H, J=4.0 Hz, anomeric H of GalN), 4.22 (ddd, 1H, J$_1$=1.0 Hz, J$_2$=5.5 Hz, J$_3$=13.0 Hz), 4.15 (dd, 1H, J$_1$=3.5 Hz, J$_2$=11.0 Hz), 4.07 (dd, 1H, J$_1$=5.0 Hz, J$_2$=8.0 Hz), 4.03-4.00 (m, 2H), 3.96-3.81 (m, 5H), 3.75-3.62 (m, 4H), 3.56 (dd, 1H, J$_1$=1.5 Hz, J$_2$=9.0 Hz), 2.73 (dd, 1H, J$_1$=5.0 Hz, J$_2$=12.5 Hz, siaH-3 eq), 2.30 (q, 4H, J=7.5 Hz), 1.68 (t, 1H, J=12.5 Hz, siaH-3ax), 1.17 (t, 6H, J=7.5 Hz); $^{13}$C-NMR (75 MHz, D$_2$O) δ 134.13, 118.69, 100.91, 96.74, 73.14, 72.30, 70.09, 69.26, 69.05, 68.79, 68.68, 68.00, 64.32, 63.11, 52.25, 50.29, 40.89, 29.79, 29.64, 10.10, 10.07; HRMS (m/z): [M+Na]$^+$ calcd. for [C$_{24}$H$_{40}$N$_2$NaO$_{14}$]$^+$, 603.2372. found, 603.2378.

Embodiment 27 Synthesis of Compound 28

This compound was prepared from Compound 50 and n-butyric anhydride, affording 28 (yield=56%). The synthetic procedure was the same as that of Compound 3.

$^1$H-NMR (300 MHz, D$_2$O) δ 5.83-5.68 (m, 1H), 5.35 (d, 1H, J=17.5 Hz), 5.26 (d, 1H, J=10.5 Hz), 4.72 (d, 1H, J=3.6 Hz, anomeric H of GalN), 4.05-3.36 (m, 15H), 2.53 (dd, 1H, J$_1$=4.5 Hz, J$_2$=12.5 Hz, siaH-3 eq), 2.07 (t, 3H, J=7.2 Hz), 1.49 (t, 1H, J=12.3 Hz, siaH-3ax), 1.42 (hexad peaks, 4H, J=7.2 Hz), 0.71 (t, 6H, J=7.2 Hz); $^{13}$C-NMR(125 MHz, D$_2$O) δ 178.89, 178.41, 174.141, 134.32, 118.98, 101.12, 97.01, 73.35, 72.50, 70.28, 69.53, 69.26, 69.10, 68.83, 68.14, 64.48, 63.33, 52.50, 50.53, 41.13, 38.59, 38.36, 19.74, 13.54, 13.42; HRMS (m/z): [M+Na]$^+$ calcd. for [C$_{26}$H$_{44}$N$_2$NaO$_{14}$]$^+$, 631.2685. found, 631.2675

Embodiment 28 Synthesis of Compound 29

This compound was prepared from Compound 50 and i-butyric anhydride, affording 29 (yield=60%). The synthetic procedure was the same as that of Compound 3.

$^1$H-NMR (500 MHz, D$_2$O) δ 6.02-5.91 (m, 1H), 5.35 (dd, 1H, J$_1$=1.5 Hz, J$_2$=17.5 Hz), 5.26 (dd, 1H, J$_1$=1.0 Hz, J$_3$=10.5 Hz) 4.92 (d, 1H, J=3.5 Hz, anomeric H of GalN), 4.22 (dd, 1H, J$_1$=5.5 Hz, J$_2$=13.0 Hz), 4.14 (dd, 1H, J$_1$=3.5 Hz, J$_2$=11.0 Hz), 4.07 (dd, 1H, J$_1$=4.5 Hz, J$_2$=7.5 Hz), 4.04-4.00 (m, 2H), 3.94-3.86 (m, 5H), 3.73-3.62 (m, 4H), 3.52 (dd, 1H, J$_1$=1.5 Hz, J$_2$=9.0 Hz), 2.74 (dd, 1H, J$_1$=4.5 Hz, J$_2$=12.5 Hz, siaH-3 eq), 2.56 (heptad peaks, 1H, J=7.0 Hz), 2.46 (heptad peaks, 1H, J=7.0 Hz), 1.68 (t, 1H, J=12.5 Hz, siaH-3ax), 1.13-1.09 (m, 12H); $^{13}$C-NMR (125 MHz, D$_2$O) δ 182.93, 182.46, 174.17, 134.32, 119.01, 101.13, 96.91, 73.37, 72.49, 70.30, 69.51, 69.28, 69.08, 68.72, 68.11, 64.49, 63.31, 52.36, 50.43, 41.17, 35.96, 35.71, 19.71, 19.61, 19.18 (2C); HRMS (m/z): [M+Na]$^+$ calcd. for [C$_{26}$H$_{44}$N$_2$NaO$_{14}$]$^+$, 631.2685. found, 631.2673

Embodiment 29 Synthesis of Compound 30

This compound was prepared from Compound 50 and caproic anhydride, affording 30 (yield=77%). The synthetic procedure was the same as that of Compound 3.

$^1$H-NMR (500 MHz, D$_2$O) δ 6.01-5.91 (m, 1H), 5.35 (dd, 1H, J$_1$=17.0 Hz, J$_2$=1.0 Hz), 5.26 (d, 1H, J$_1$=10.5 Hz), 4.91 (d, 1H, J=3.5 Hz), 4.21 (dd, 1H, J$_1$=5.5 Hz, J$_2$=13.0 Hz), 4.16 (dd, 1H, J$_1$=5.5 Hz, J$_2$=13.0 Hz), 4.07 (dd, 1H, J$_1$=4.0 Hz, J$_2$=8.0 Hz), 4.02-3.99 (m, 2H), 3.93-3.79 (m, 5H), 3.71-3.61 (m, 4H), 3.55 (d, 1H, J=7.0 Hz), 2.72 (dd, 1H, J$_1$=5.0 Hz, J$_2$=13.0 Hz, siaH-3 eq), 2.31-2.25 (m, 4H), 1.68 (t, 1H, J=12.5 Hz siaH-3ax), 1.62-1.57 (m, 4H), 1.36-1.24 (m, 8H), 0.86 (m, 6H); $^{13}$C-NMR(125 MHz, D$_2$O) δ 178.94, 178.48, 173.36, 134.11, 118.81, 100.51, 96.85, 73.28, 72.10, 70.08, 69.38, 69.10, 68.98, 68.40, 67.96, 64.35, 63.31, 52.27, 50.34, 40.68, 36.46, 36.26, 31.08, 30.96, 25.66, 22.25, 13.78; HRMS (m/z): [M+H]$^+$ calcd. for [C$_{30}$H$_{53}$N$_2$O$_{14}$]$^+$, 665.3491. found, 665.3495

Embodiment 30 Synthesis of Compound 31

This compound was prepared from Compound 50 and methyl fluoroacetate, affording 31 (yield=67%). The synthetic procedure was the same as that of Compound 7.

$^1$H-NMR (500 MHz, D$_2$O) δ 5.90-5.85 (m, 1H), 5.27 (dd, 1H, J$_1$=1.5 Hz, J$_2$=17.0 Hz), 5.27 (d, 1H, J=10.5 Hz), 4.87 (d, 1H, J=3.0 Hz, anomeric H of GalN), 4.8 (d, 2H, J$_{F-H}$=46.0 Hz), 4.7 (d, 2H, J$_{F-H}$=46.0 Hz), 4.17 (dd, 1H, J$_1$=4.0 Hz, J$_2$=10.5 Hz), 4.13 (dd, 1H, J$_1$=5.0 Hz, J$_2$=12.5 Hz), 4.00 (dd, 1H, J$_1$=4.0 Hz, J$_2$=8.0 Hz), 3.96-3.72 (m, 8H), 3.65 (ddd, 1H, J$_1$=4.5 Hz, J$_2$=10.0 Hz, J$_3$=12.0 Hz), 3.57-3.49 (m, 2H), 3.50 (dd, 1H, J$_1$=1.5 Hz, J$_2$=9.0 Hz), 2.72 (dd, 1H, J$_1$=4.5 Hz, J$_2$=12.5 Hz, siaH-3 eq), 1.79 (t, 1H, J$_1$=J$_2$=12.5 Hz, siaH-3ax); $^{13}$C-NMR (125 MHz, D$_2$O) δ 175.36, 171.5 (d, 1C, J$_{F-C}$=18.12 Hz), 171.1 (d, 1C, J$_{F-C}$=18.62 Hz), 133.65, 118.22, 100.44, 96.19, 80 (d, 1C, J$_{F-C}$=189.53 Hz), 79 (d, 1C, J$_{F-C}$=179.56 Hz), 72.21, 71.87, 69.62, 68.79, 68.51, 68.149, 68.08, 67.40, 63.77, 62.66, 51.50, 49.58, 40.27; HRMS (m/z): [M+Na]$^+$ calcd. for [C$_{22}$H$_{32}$F$_4$N$_2$O$_{14}$]$^+$, 611.1870. found, 611.1872

Embodiment 31 Synthesis of Compound 32

This compound was prepared from Compound 50 and methyl difluoroacetate, affording 32 (yield=72%). The synthetic procedure was the same as that of Compound 7.

$^1$H-NMR (500 MHz, D$_2$O) δ 6.10 (t, 1H, J$_{F-H}$=53.6 Hz), 6.09 (dd, 1H, J$_{F-H}$=53.6 Hz), 5.92-5.86 (m, 1H), 5.30 (d, 1H, J=17.5 Hz), 5.18 (d, 1H, J=10.5 Hz), 4.91 (d, 1H, J=3.5 Hz, anomeric H of Gal), 4.20-4.13 (m, 2H), 4.02 (dd, 1H, J$_1$=4.5 Hz, J$_3$=8.0 Hz), 4.00-3.78 (m, 9H), 3.71-3.65 (m, 1H), 3.58-3.54 (m, 1H), 3.49 (d, 1H, J=9.0 Hz), 2.67 (dd, 1H, J$_1$=4.5 Hz, J$_2$=12.5 Hz, siaH-3 eq), 1.69 (dd, 1H, J$_1$=J$_2$=12.5 Hz, siaH-3ax); $^{13}$C-NMR(125 MHz, D$_2$O) δ 173.33, 165.3 (m, 2C), 133.61, 118.26, 108.29 (t, 1C, J$_{F-C}$=46.5 Hz), 108.17 (t, 1C, J$_{F-C}$=5.6 Hz), 100.45, 95.86, 71.99, 71.91, 69.63, 68.81, 68.48, 68.16, 68.02, 67.21, 63.78, 51.91, 50.14, 40.24; HRMS (m/z): [M+Na]$^+$ calcd. for [C$_{22}$H$_{32}$F$_4$N$_2$O$_{14}$]$^+$, 647.1682. found, 647.1669

Embodiment 32 Synthesis of Compound 33

This compound was prepared from Compound 50 and methyl trifluoroacetate, affording 33 (yield=49%). The synthetic procedure was the same as that of Compound 7.

$^1$H-NMR (500 MHz, D$_2$O) δ 6.01-5.92 (m, 1H), 5.35 (dq, 1H, J=1.5 Hz, 17.5 Hz), 5.26 (dd, 1H, J$_1$=1.5 Hz, J$_3$=10.5 Hz), 5.01 (d, 1H, J=4.0 Hz, anomeric H of GalN), 4.21-4.27 (m, 2H), 4.11 (dd, 1H, J$_1$=4.0 Hz, J$_2$=8.0 Hz), 4.07-3.86 (m, 8H), 3.76 (ddd, 1H, J$_1$=4.5 Hz, J$_2$=9.5 Hz, J$_3$=12.0 Hz), 3.67-3.61 (m, 2H), 3.56 (dd, 1H, J$_1$=1.5, J$_2$=9.0 Hz), 2.76 (dd, 1H, J$_1$=4.5 Hz, J$_2$=12.5 Hz, siaH-3 eq), 1.72 (t, 1H, J=12.5 Hz, siaH-3ax); $^{13}$C-NMR(125 MHz, D$_2$O) δ 174.04, 160.1 (m, 2C), 134.28, 119.01, 116.51 (dd, 2C, J$_{F-H}$=285.12 Hz), 101.18, 96.36, 72.66, 72.51, 70.35, 69.54, 69.19, 68.91, 68.65, 67.68, 64.53, 63.32, 53.13, 51.46, 40.99; HRMS (m/z): [M+Na]$^+$ calcd. for [C$_{22}$H$_{30}$F$_6$N$_2$O$_{14}$]$^+$, 683.1493. found, 683.1501

Embodiment 33 Synthesis of Compound 34

This compound was prepared from Compound 50 and chloroacetic acid, affording 34 (yield=60%). The synthetic procedure was the same as that of Compound 10.

$^1$H-NMR (500 MHz, D$_2$O) δ 6.02-5.93 (m, 1H), 5.35 (dq, 1H, J=1.5 Hz, 17.5 Hz), 5.27 (dq, 1H, J=1.5 Hz, 10.5 Hz), 4.97 (d, 1H, J=4.0 Hz, anomeric H of GalN), 4.21-4.18 (m, 2H), 4.19-4.17 (m, 3H), 4.09 (dd, 1H, J$_1$=4.0 Hz, J$_3$=8.5 Hz), 4.06-4.01 (m, 2H), 3.93-3.86 (m, 5H), 3.78 (ddd, 1H, J$_1$=4.5 Hz, J$_2$=9.5 Hz, J$_3$=12.0 Hz), 3.68 (dd, 1H, J$_1$=4.5 Hz, J$_3$=10.5 Hz), 3.65 (dd, 1H, J$_1$=6.5 Hz, J$_3$=12.0 Hz), 3.58 (dd, 1H, J$_1$=1.5 Hz, J$_3$=9.0 Hz), 2.71 (dd, 1H, J$_1$=4.5 Hz, J$_2$=12.5 Hz, siaH-3 eq), 1.75 (t, J=12.0 Hz, siaH-3ax); $^{13}$C-NMR (125 MHz, D$_2$O) δ 173.29, 171.20, 170.86, 134.33, 118.98, 100.58, 96.79, 73.10, 72.24, 70.31, 69.57, 69.24, 68.98, 68.46, 68.21, 64.52, 63.49, 52.97, 51.09, 43.05, 42.97, 40.62; HRMS (m/z): [M+Na]$^+$ calcd. for [C$_{22}$H$_{34}$Cl$_2$N$_2$NaO$_{14}$]$^+$, 643.1279. found, 643.1306

Embodiment 34 Synthesis of Compound 35

This compound was prepared from Compound 50 and methyl dichloroacetate, affording 35 (yield=43%). The synthetic procedure was the same as that of Compound 7.

$^1$H-NMR (500 MHz, D$_2$O) δ 6.35 (s, 1H), 6.32 (s, 1H), 6.01-5.92 (m, 1H), 5.35 (dq, 1H, J=1.5 Hz, 17.5 Hz), 5.26 (dq, 1H, J=1.5 Hz, 10.5 Hz), 4.92 (d, 1H, J=3.5 Hz, anomeric H of GalN), 4.22 (ddt, 1H, J$_1$=J$_2$=1.5 Hz, J$_3$=5.5 Hz, J$_4$=13.0 Hz), 4.18 (dd, 1H, J$_1$=3.5 Hz, J$_2$=11.0 Hz), 4.10 (dd, 1H, J$_1$=4.5 Hz, J$_2$=8.0 Hz), 4.08-3.84 (m, 8H), 3.75 (ddd, 1H, J$_1$=4.5 Hz, J$_2$=9.0 Hz, J$_3$=12.0 Hz), 3.66-3.61 (m, 2H), 3.57 (dd, 1H, J$_1$=1.5 Hz, J$_2$=9.5 Hz), 2.74 (dd, 1H, J$_1$=5.0 Hz, J$_2$=12.5 Hz, siaH-3 eq), 1.69 (t, 1H, J=12.0 Hz, siaH-3ax); $^{13}$C-NMR (125 MHz, D$_2$O) δ 173.99, 168.21, 168.04, 134.29, 119.14, 101.10, 96.41, 72.89, 72.65, 70.37, 69.60, 69.25, 69.08, 68.67, 68.03, 66.96, 66.76, 64.52, 63.36, 53.32, 51.64, 41.04; HRMS (m/z): [M+H]$^+$ calcd. for [C$_{22}$H$_{33}$Cl$_4$N$_2$O$_{14}$]$^+$, 689.0680. found, 689.0671

Embodiment 35 Synthesis of Compound 36

This compound was prepared from Compound 50 and methyl trichloroacetate, affording 36 (yield=64%). The synthetic procedure was the same as that of Compound 7.

$^1$H-NMR (500 MHz, D$_2$O) δ 6.01-5.91 (m, 1H), 5.35 (dq, 1H, J=1.5 Hz, 17.5 Hz), 5.26 (dd, 1H, J$_1$=1.5 Hz, J$_2$=10.5 Hz), 5.01 (d, 1H, J=3.5 Hz, anomeric H of GalN), 4.25 (ddt, 1H, J$_1$=J$_2$=1.5 Hz, J$_3$=5.0 Hz, J$_4$=13.0 Hz), 4.20 (dd, 1H, J$_1$=3.5 Hz, J$_2$=11.0 Hz), 4.14-3.80 (m, 10H), 3.66 (dd, 1H, J$_1$=4.0 Hz, J$_2$=11.0 Hz), 3.63 (dd, 1H, J$_1$=6.5 Hz, J$_2$=11.5 Hz), 3.59 (dd, 1H, J$_1$=1.5 Hz, J$_2$=9.5 Hz), 2.76 (dd, 1H, J$_1$=4.5 Hz, J$_2$=12.5 Hz, siaH-3 eq), 1.72 (t, 1H, J$_1$=J$_{2=12.5}$ Hz, siaH-3ax); $^{13}$C-NMR(75 MHz, D$_2$O) δ 173.96, 165.38, 134.06, 119.05, 100.98, 96.14, 72.60, 72.46, 70.26, 69.47, 69.18, 69.18, 69.01, 68.27, 67.56, 64.41, 63.14, 54.42, 52.84, 41.14; HRMS (m/z): [M+Na]$^+$ calcd. for [C$_{22}$H$_{30}$Cl$_6$N$_2$NaO$_{14}$]$^+$, 778.9720. found, 778.9698

Embodiment 36 Synthesis of Compound 37

Compound 39 (For its synthesis, see Embodiment 38) (18.0 mg, 0.032 mmol) was dissolved in 5 ml methanol, 50% NH$_2$OH/water (0.5 mL, 7.57 mmol) and KCN (1.0 mg, 0.016 mmol) were added. The mixture was stirred at R.T. for 20 h. The mixture was concentrated in vacuum. The residue was purified by C18 reverse-phase column chromatography with MeOH/water as eluent and then on a on a Biogel P-2 column with water as the eluent, affording 37 (yield=50%).

$^1$H-NMR (500 MHz, D$_2$O) δ 6.01-5.93 (m, 1H), 5.36 (d, 1H, J$_1$=17.0 Hz), 5.26 (d, 1H, J$_1$=10.5 Hz), 4.92 (d, 1H, J=4.0 Hz, anomeric H of GalN), 4.20 (ddd, 1H, J$_1$=1.0 Hz, J$_2$=5.5 Hz, J$_3$=13.0 Hz), 4.15 (dd, 1H, J$_1$=3.5 Hz, J$_2$=11.0 Hz), 4.06 (dd, 1H, J$_1$=4.0 Hz, J$_2$=8.0 Hz), 4.04-3.98 (m, 2H), 3.96-3.82 (m, 5H), 3.79-3.72 (m, 2H), 3.71-3.62 (m, 3H), 2.73 (dd, 1H, J$_1$=4.5 Hz, J$_2$=13.5 Hz, siaH-3 eq), 2.03 (s, 6H), 1.83 (t, 1H, J$_1$=J$_2$=12.5 Hz, siaH-3ax); $^{13}$C-NMR (125 MHz, D$_2$O) δ 175.64, 175.22, 166.20, 134.26, 118.61, 100.03, 96.91, 74.23, 71.78, 70.02, 69.34, 69.08, 68.28, 68.14, 67.62, 63.76, 63.44, 52.16, 50.41, 39.13, 22.64, 22.52; HRMS (m/z): [M+Na]$^+$ calcd. for [C$_{22}$H$_{37}$N$_3$NaO$_{14}$]$^+$, 590.2168. found, 590.2163

Embodiment 37 Synthesis of Compound 38

Compound 39 (For its synthesis, see Embodiment 38) (10.0 mg, 0.017 mmol) was dissolved in 2 ml methanol, NaBH$_4$ (6.0 mg, 0.158 mmol) was added in three batches. The mixture was stirred at R.T. for 1 h. The mixture was concentrated in vacuum. The residue was purified by C18 reverse-phase column chromatography with MeOH/water as eluent and then on a on a Biogel P-2 column with water as the eluent, affording 38 (yield=94%).

$^1$H-NMR (500 MHz, D$_2$O) δ 6.02-5.92 (m, 1H), 5.34 (dd, 1H, J$_1$=1.5 Hz, J$_2$=12.5 Hz), 5.25 (d, 1H, J=10.5 Hz), 4.94 (d, 1H, J=3.5 Hz, anomeric H of GalN), 4.21 (ddd, 1H, J$_1$=1.0 Hz, J$_2$=5.5 Hz, J$_3$=13.0 Hz), 4.16 (dd, 1H, J$_1$=3.5 Hz, J$_2$=11.0 Hz), 4.08-4.00 (m, 3H), 3.95-3.78 (m, 8H), 3.74-3.68 (m, 2H), 3.62 (dd, 1H, J$_1$=6.0 Hz, J$_2$=12.0 Hz), 3.52 (d, 1H, J=9.0 Hz), 2.30 (dd, 1H, J$_1$=5.5 Hz, J$_2$=13.5 Hz, siaH-3 eq), 2.04 (s, 3H), 2.03 (s, 3H), 1.75 (t, 1H, J=13.0 Hz, siaH-3ax); $^{13}$C-NMR (125 MHz, D$_2$O) δ 177.44, 177.09, 136.14, 120.44, 102.79, 98.77, 74.09, 73.07, 72.25, 71.21, 71.04, 70.80, 70.25, 70.08, 65.59, 63.56, 62.79, 54.69, 52.33, 38.67, 24.54, 24.38. HRMS (m/z): [M+Na]$^+$ calcd. for [C$_{22}$H$_{38}$N$_2$NaO$_{13}$]$^+$, 561.2266. found, 561.2267

Embodiment 38 Synthesis of Compound 39

Compound 48 (For its synthesis, see Embodiment 42) (100 mg, 0.119 mmol) was dissolved in 10 ml methanol, NaOMe/MeOH (30%, 0.02 g, 011 mmol) was added. The mixture was stirred at R.T. for 4 h. The reaction mixture was neutralized with 1N HCl/MeOH to pH=6. The mixture was concentrated in vacuum. The residue was purified by C18 reverse-phase column chromatography with MeOH/water as the eluent. Fractions containing the expected product were collected to afford 39 (yield=95%).

$^1$H-NMR (500 MHz, D$_2$O) δ 6.02-5.92 (m, 1H), 5.35 (dq, 1H, J=1.5 Hz, 17.5 Hz), 5.27 (dd, 1H, J$_1$=1.5 Hz, J$_2$=10.5 Hz), 4.92 (d, 1H, J=3.5 Hz, anomeric H of GalN), 4.21-4.14 (m, 2H), 4.06-3.96 (m, 4H), 3.93-3.83 (m, 8H), 3.7 (ddd, 1H, J$_1$=4.5 Hz, J$_2$=10.0 Hz, J$_3$=12.0 Hz), 3.71-3.64 (m, 2H), 3.56 (d, 1H, J=9.5 Hz), 2.71 (dd, 1H, J$_1$=4.5 Hz, J$_3$=13.0 Hz, siaH-3 eq), 2.04 (s, 6H), 1.83 (t, J$_1$=J$_2$=12.5 Hz, siaH-3ax); $^{13}$C-NMR (125 MHz, D$_2$O) δ 175.70, 175.36, 170.58, 134.36, 118.79, 99.64, 97.06, 73.62, 71.30, 70.10, 69.51, 69.25, 69.01, 68.31, 67.89, 64.55, 63.85, 54.16, 52.44, 50.53, 39.83, 22.82, 22.64; HRMS (m/z): [M+Na]$^+$ calcd. for [C$_{23}$H$_{38}$N$_2$NaO$_{14}$]$^+$, 589.2215. found, 589.2223

Embodiment 39 Synthesis of Compound 40

This compound was prepared from Compound 61 (For its synthesis, see Embodiment 47), affording 40 (yield=95%). The synthetic procedure was the same as that of Compound 3.

$^1$H-NMR (500 MHz, D$_2$O) δ 6.04-5.95 (m, 1H), 5.38 (dq, 1H, J=1.5 Hz, 17.5 Hz), 5.28 (dd, 1H, J$_1$=1.5 Hz, J$_2$=10.5 Hz), 4.97 (d, 1H, J=3.5 Hz, anomeric H of Gal), 4.21 (ddd, 1H, J$_1$=1.0 Hz, J$_2$=5.5 Hz, J$_3$=13.0 Hz), 4.16 (dd, 1H, J$_1$=3.5 Hz, J$_2$=11.0 Hz), 4.10-4.02 (m, 2H), 3.98 (d, 1H, J=2.5 Hz), 3.96-3.60 (m, 9H), 3.58 (dd, 1H, J$_1$=1.5 Hz, J$_2$=8.5 Hz), 2.72 (dd, 1H, J$_1$=4.5 Hz, J$_3$=13.0 Hz, siaH-3 eq), 2.03 (s, 3H), 1.74 (t, J=12.5 Hz, siaH-3ax); $^{13}$C-NMR (125 MHz, D$_2$O) δ 175.76, 173.21, 134.35, 119.10, 100.47, 98.31, 73.45, 72.13, 70.07, 70.00, 69.54, 69.02, 68.85, 68.63, 64.45, 63.51, 52.55, 40.56, 22.80; HRMS (m/z): [M+Na]$^+$ calcd. for [C$_{20}$H$_{33}$NNaO$_{14}$]$^+$, 534.1793. found, 534.1789

Embodiment 40 Synthesis of Compound 41

This compound was prepared from Compound 63 (For its synthesis, see Embodiment 48), affording 41 (yield=95%). The synthetic procedure was the same as that of Compound 3.

$^1$H-NMR (500 MHz, D$_2$O) δ 6.01-5.92 (m, 1H), 5.35 (dq, 1H, J=1.5 Hz, 17.0 Hz), 5.28 (dd, 1H, J$_1$=1.5 Hz, J$_2$=10.5 Hz), 4.97 (d, 1H, J=3.5 Hz, anomeric H of GlcNAc), 4.21 (ddd, 1H, J$_1$=1.5 Hz, J$_2$=5.0 Hz, J$_3$=13.0 Hz), 4.02 (ddd, 1H, J$_1$=1.5 Hz, J$_2$=6.0 Hz, J$_3$=13.0 Hz), 3.98 (dd, 1H, J$_1$=5.0 Hz, J$_2$=10.5 Hz), 3.93 (dd, 1H, J$_1$=4.0 Hz, J$_2$=10.5 Hz), 3.91-3.79 (m, 4H), 3.78-3.61 (m, 5H), 3.59 (dd, 1H, J$_1$=1.5 Hz, J$_2$=9.0 Hz), 3.53 (dd, 1H, J$_1$=9.5 Hz, J$_2$=10.0 Hz), 2.75 (dd, 1H, J$_1$=4.5 Hz, J$_2$=12.0 Hz, siaH-3 eq), 2.04 (s, 3H), 1.71 (t, J=12.0 Hz, siaH-3ax); $^{13}$C-NMR (125 MHz, D$_2$O) δ 175.80, 175.16, 174.15, 134.32, 118.80, 100.89, 96.77, 73.24, 72.51, 71.75, 71.32, 70.68, 69.38, 69.00, 63.56, 63.36, 54.31, 52.63, 40.87, 22.76, 22.58; HRMS (m/z): [M+Na]$^+$ calcd. for [C$_{22}$H$_{36}$N$_2$NaO$_{14}$]$^+$, 575.2059. found, 575.2067

Embodiment 41 Synthesis of Compound 42

This compound was prepared from Compound 49 (For its synthesis, see Embodiment 42), affording 42 (yield=95%). The synthetic procedure was the same as that of Compound 3.

$^1$H-NMR (500 MHz, D$_2$O) δ 6.02-5.94 (m, 1H), 5.35 (dd, 1H, J$_1$=17.0 Hz,), 5.26 (d, 1H, J$_1$=10.5 Hz), 4.95 (d, 1H, J=3.5 Hz, anomeric Hon GalNAc), 4.21 (dd, 1H, J$_1$=5.0 Hz, J$_2$=13.0 Hz), 4.18 (dd, 1H, J$_1$=4.5 Hz, J$_2$=8.5 Hz), 4.11-4.02 (m, 4H), 3.93-3.83 (m, 5H), 2.75 (dd, 1H, J$_1$=5.5 Hz, J$_2$=10.0 Hz), 3.76 (dd, 1H, J$_1$=5.5 Hz, J$_2$=12.0 Hz), 3.56 (d, 1H, J=9.0 Hz), 3.47 (dd, 1H, J$_1$=8.5 Hz, J$_2$=10.0 Hz), 2.39 (dd, 1H, J$_1$=5.0 Hz, J$_2$=13.0 Hz, sialH-3 eq), 2.05 (s, 3H), 2.04 (s, 3H), 1.68 (dd, 1H, J$_1$=12.5 Hz, J$_2$=12.0 Hz, sialH-3ax); $^{13}$C-NMR (125 MHz, D$_2$O) δ 177.45, 177.20, 174.52, 136.43, 120.45, 101.42, 99.08, 73.28, 72.59, 72.01, 71.44, 71.27, 70.52, 70.24, 69.11, 65.92, 65.00, 54.50, 52.45, 41.92, 24.70, 24.53; HRMS (m/z): [M+Na]$^+$ calcd. for C$_{22}$H$_{36}$N$_2$NaO$_{14}$, 575.2059. found, 575.2050

Embodiment 42 Synthesis of Compound 48 and 49

Compound 46 (1.07 g, 2.93 mmol, 1.00 eq. For its synthesis, see U.S. Pat. No. 6,013,779.) and Compound 47 (2.06 g, 3.38 mmol, 1.15 eq. For its synthesis, see J. Org. Chem. 2000, 65, 144-151.) were added into the 100 mL double-necked flask together with activated molecular sieves. Under argon atmosphere, 40 mL THF was added. The mixture was stirred at R.T. for 0.5 h and then was cooled to −72° C. To the mixture, TMSOTf (70 μL, 0.36 mmol, 0.11 eq.) was added in three batches during 15 min. The reaction went to completion in 4 h (by TLC monitoring). TEA (1.0 mL) was added. The mixture was filtered through diatomite. The filtrate was concentrated in vacuum. The residue was purified on silica gel, affording 48 and 49 (48:49=1:1.2, yield=84%).

Compound 48: $^1$H-NMR (500 MHz, CDCl$_3$) δ 8.08-8.05 (m, 2H), 7.60-7.50 (m, 1H), 7.50-7.40 (m, 2H), 5.97-5.87 (m, 1H), 5.75 (d, 1H, J=10.0 Hz, NHAc), 5.42 (d, 1H, J=10.0 Hz, NHAc), 5.40-5.31 (m, 3H), 5.29 (dd, 1H, J$_1$=3.0 Hz, J$_2$=11.0 Hz), 5.23 (ddd, 1H, J$_1$=1.0 Hz, J$_2$=3.0 Hz, J$_3$=10.5 Hz), 4.96 (d, 1H, J=3.5 Hz, anomeric H of GalNAc), 4.92-4.85 (m, 2H), 4.36 (dd, 1H, J$_1$=2.5 Hz, J$_2$=12.5 Hz), 4.25-4.20 (m, 2H), 4.18-4.00 (m, 5H), 3.88 (dd, 1H, J$_1$=5.5 Hz, J$_2$=10.0 Hz), 3.80 (s, 3H), 3.75 (dd, 1H, J$_1$=7.0 Hz, J$_2$=10.0 Hz), 3.02 (d, 1H, J=3.0 Hz, OH), 2.59 (dd, 1H, J$_1$=5.0 Hz, J$_2$=13.0 Hz, sialH-3 eq), 2.14 (s, 3H, OAc), 2.11 (s, 3H, OAc), 2.01 (s, 3H, OAc), 1.98 (t, 1H, J=13.0 Hz, sialH-3ax), 1.97 (s, 3H, OAc), 1.88 (s, 3H, NAc), 1.87 (s, 3H, NAc); $^{13}$C-NMR (125 MHz, CDCl$_3$) δ 170.93, 170.86, 170.25, 170.18, 170.15, 169.92, 168.03, 166.67, 133.53, 133.31, 129.92, 129.52, 128.46, 117.90, 98.70, 96.96, 72.78, 72.19, 69.10, 69.03, 68.68, 68.36, 67.40, 66.89, 62.96, 62.54, 23.30, 23.13, 21.03, 20.82, 20.77, 20.63. HRMS (m/z): [M+Na]$^+$ calcd. for [C$_{38}$H$_{50}$N$_2$NaO$_{19}$]$^+$, 861.2900. found, 861.2903

Compound 49: $^1$H-NMR (500 MHz, CDCl$_3$) δ 8.12-8.08 (m, 2H), 7.60-7.52 (m, 1H), 7.47-7.40 (m, 2H), 5.96-5.84 (m, 2H), 5.62 (d, 1H, J=10.0 Hz, NHAc), 5.44-5.28 (m, 5H), 5.23 (dd, 1H, $J_1$=1.5 Hz, $J_2$=10.5 Hz), 4.94 (d, 1H, J=3.5 Hz, anomeric H of GalNAc), 4.85 (ddd, 1H, $J_1$=4.0 Hz, $J_2$=10.0 Hz, $J_3$=11.0 Hz), 4.78 (dd, 1H, $J_1$=2.0 Hz, $J_2$=12.5 Hz), 4.40-4.32 (m, 2H), 4.21 (ddt, 1H, $J_1$=$J_2$=1.0 Hz, $J_3$=5.0 Hz, $J_4$=12.5 Hz), 4.16 (dd, 1H, $J_1$=8.0 Hz, $J_2$=12.5 Hz), 4.11 (dd, 1H, $J_1$=5.0 Hz, $J_2$=8.5 Hz), 4.02-3.96 (dd, 1H, $J_1$=6.0 Hz, $J_2$=12.0 Hz), 3.88 (t, 1H, $J_1$=$J_2$=9.0 Hz), 3.82 (s, 3H), 3.82-3.72 (m, 1H), 3.57 (d, 1H, J=4.0 Hz, OH), 3.50 (dd, 1H, $J_1$=5.0 Hz, $J_2$=9.0 Hz), 2.51 (dd, 1H, $J_1$=5.0 Hz, $J_2$=13.0 Hz, sialH-3 eq), 2.14 (s, 3H, OAc), 2.16-2.10 (1H, overlapped, sialH-3ax), 2.11 (s, 3H, OAc), 2.05 (s, 3H, OAc), 1.98 (s, 3H, OAc), 1.85 (s, 3H, NAc), 1.80 (s, 3H, NAc); $^{13}$C-NMR (125 MHz, CDCl$_3$) δ 171.43, 170.77, 170.47, 170.00, 167.13, 166.73, 133.54, 133.31, 129.97, 129.44, 128.40, 117.63, 98.29, 97.08, 72.07, 71.59, 70.95, 68.88, 68.38, 68.23, 68.11, 66.46, 62.45, 61.57, 52.77, 49.90, 47.83, 37.41, 23.19, 23.14, 21.09, 20.85, 20.81, 20.75. HRMS (m/z): [M+Na]$^+$ calcd. for [C$_{38}$H$_{50}$N$_2$NaO$_{19}$]$^+$, 861.2900. found, 861.2882

Embodiment 43 Synthesis of Compound 50

Compound 48 (100 mg, 0.119 mmol) was dissolved in 10 ml methanol (10 mg/mL), NaOMe/MeOH (30%, 0.02 g, 011 mmol) was added. The mixture was stirred at R.T. for 4 h. The mixture was heated to 90° C. and stirred for 8 h. The reaction mixture was neutralized with 1N HCl/MeOH to pH=4-7. The mixture was concentrated in vacuum. The residue was purified on a Biogel P-2 column with water as the eluent. Fractions containing the expected product were collected to afford 50 (yield=88%).

$^1$H-NMR (500 MHz, D$_2$O) δ 6.02-5.96 (m, 1H), 5.37 (ddd, 1H, $J_1$=1.5 Hz, $J_2$=3.0 Hz, $J_3$=17.5 Hz), 5.29 (dd, 1H, $J_1$=1.5 Hz, $J_2$=10.5 Hz), 5.11 (d, 1H, J=3.5 Hz, anomeric H of GalN), 4.26 (dd, 1H, $J_1$=5.5 Hz, $J_2$=12.5 Hz), 4.09-4.05 (m, 2H), 3.99-3.96 (m, 2H), 3.93-3.88 (m, 3H), 3.80 (dd, 1H, $J_1$=2.0 Hz, $J_2$=9.0 Hz), 3.73-3.68 (m, 2H), 3.61 (dd, 1H, $J_1$=4.0 Hz, $J_2$=10.5 Hz), 3.57-3.54 (m, 1H), 3.38-3.35 (m, 1H), 2.95-2.91 (m, 1H), 2.72 (dd, 1H, $J_1$=4.5 Hz, $J_2$=12.5 Hz, sialH-3 eq), 1.64 (t, 1H, J=12.5 Hz, sialH-3ax); $^{13}$C-NMR (75 MHz, D$_2$O) δ 176.08, 135.91, 121.21, 102.96, 8.07, 76.19, 74.57, 72.38, 71.83, 71.58, 70.82, 70.60, 70.18, 66.26, 65.07, 54.99, 53.35, 42.87; HRMS (m/z): [M+Na]$^+$ calcd. for [C$_{18}$H$_{32}$N$_2$NaO$_{12}$]$^+$, 491.1847. found, 491.1852

Embodiment 44 Synthesis of Compound 52 and 55

These compounds were prepared from Compound 51 (For its synthesis, see U.S. Pat. No. 6,013,779) and Compound 46 (For its synthesis, see U.S. Pat. No. 6,013,779), affording 52 and 55 (52:55=2.6:1, yield=81%). The synthetic procedure was the same as that of Compound 48 and 49.

Compound 52: $^1$H-NMR (500 MHz, CDCl$_3$) δ 8.08-8.04 (m, 2H), 7.60-7.52 (m, 1H), 7.50-7.39 (m, 2H), 7.10 (d, 1H, J=10.0 Hz, NHTFA), 5.98-5.87 (m, 1H), 5.78 (d, 1H, J=10.0 Hz, NHAc), 5.38-5.27 (m, 4H), 5.25 (dd, 1H, $J_1$=1.0 Hz, $J_2$=10.0 Hz), 5.23 (ddd, 1H, $J_1$=4.5 Hz, $J_2$=10.5 Hz, $J_3$=12.0 Hz), 4.96 (d, 1H, J=3.5 Hz, anomeric H of GalNAc), 4.88 (ddd, 1H, $J_1$=4.0 Hz, $J_2$=10.0 Hz, $J_3$=11.0 Hz), 4.38 (dd, 1H, $J_1$=2.0 Hz, $J_2$=12.5 Hz), 4.30 (dd, 1H, $J_1$=2.0 Hz, $J_2$=12.5 Hz), 4.25-4.20 (m, 2H), 4.08 (dd, 1H, $J_1$=6.0 Hz, $J_2$=12.5 Hz), 4.06-4.00 (m, 3H), 3.88 (dd, 1H, $J_1$=5.5 Hz, $J_2$=9.5 Hz), 3.80 (s, 3H, COOMe), 3.78 (dd, 1H, $J_1$=7.0 Hz, $J_2$=9.5 Hz), 3.08 (d, 1H, J=3.0 Hz, OH), 2.63 (dd, 1H, $J_1$=5.0 Hz, $J_2$=13.0 Hz, sialH-3 eq), 2.14 (s, 3H, OAc), 2.11 (s, 3H, OAc), 2.12 (s, 3H, OAc), 1.97 (t, 1H, $J_1$=$J_2$=12.5 Hz sialH-3ax), 1.99 (s, 3H, OAc), 1.96 (s, 3H, OAc), 1.88 (s, 3H, NAc); $^{13}$C-NMR (125 MHz, CDCl$_3$) δ 170.90, 170.86, 170.43, 169.94, 167.86, 166.86, 157.59 (q, 1C, J=37.7 Hz, carbonyl in TFA) 133.51, 133.37, 129.89, 129.46, 128.46, 117.92, 115.05 (q, 1C, J=286.2 Hz, CF$_3$), 98.70, 96.96, 72.21, 71.99, 69.31, 68.71, 68.47, 68.38, 67.26, 66.84, 63.06, 62.38, 53.10, 49.91, 47.32, 37.10, 23.24, 21.00, 20.59, 20.57, 20.54; HRMS (m/z): [M+Na]$^+$ calcd. for [C$_{38}$H$_{47}$F$_3$N$_2$NaO$_{19}$]$^+$, 915.2617. found, 915.2615.

Compound 55: $^1$H-NMR (500 MHz, CDCl$_3$) δ 8.10-8.04 (m, 2H), 7.56 (t, 1H, J=7.5 Hz), 7.43 (q, 2H, J=8.0 Hz), 5.98-5.87 (m, 1H), 5.88 (d, 1H, J=10.0 Hz, NHTFA), 5.42-5.28 (m, 4H), 5.25 (dd, 1H, $J_1$=1.0 Hz, $J_2$=10.0 Hz), 4.96 (d, 1H, J=3.5 Hz, anomeric H of GalNAc), 4.84 (ddd, 1H, $J_1$=4.0 Hz, $J_2$=10.0 Hz, $J_3$=11.0 Hz), 4.78 (dd, 1H, $J_1$=2.0 Hz, $J_2$=12.0 Hz), 4.46 (dd, 1H, $J_1$=2.0 Hz, $J_2$=10.5 Hz), 4.35 (br, 1H), 4.21 (dd, 1H, $J_1$=5.0 Hz, $J_2$=12.5 Hz), 4.14 (dd, 1H, $J_1$=8.0 Hz, $J_2$=12.0 Hz), 4.10 (dd, 1H, $J_1$=5.0 Hz, $J_2$=8.0 Hz), 4.00 (dd, 1H, $J_1$=5.5 Hz, $J_2$=12.5 Hz), 3.96-3.88 (m, 2H), 3.83 (s, 3H, COOMe), 3.58-3.50 (m, 2H), 3.45-3.87 (br, 1H), 2.54 (dd, 1H, $J_1$=5.0 Hz, $J_2$=13.0 Hz, sialH-3 eq), 2.26 (br, 1H) 2.13 (s, 3H, OAc), 2.07 (s, 3H, OAc), 2.05 (s, 3H, OAc), 1.99 (s, 3H, OAc), 1.96 (s, 3H, OAc), 1.86 (s, 3H, NAc), 1.86 (t, 1H, $J_1$=$J_2$=12.5 Hz, overlapped, sialH-3ax); $^{13}$C-NMR (75 MHz, CDCl$_3$) δ 171.56, 170.84, 170.64, 170.27, 170.20, 166.89, 157.76 (q, 1C, J=37.7 Hz, carbonyl in TFA), 133.48, 129.95, 129.29, 128.51, 117.87, 115.40 (q, 1C, J=285.7 Hz, CF$_3$) 98.30, 97.05, 72.09, 71.81, 70.57, 68.67, 68.48, 68.03, 67.88, 66.53, 62.31, 61.69, 52.92, 50.13, 47.70, 37.35, 23.22, 21.02, 20.79, 20.58; HRMS (m/z): [M+Na]$^+$ calcd. for [C$_{38}$H$_{47}$F$_3$N$_2$NaO$_{19}$]$^+$, 915.2617. found, 915.2626

Embodiment 45 Synthesis of Compound 54

This compound was prepared from Compound 47 (See Tetrahedron Lett. 1992, 33, 6123-6126) and Compound 53 (For its synthesis, see Embodiment 46), affording 54 (yield=58%). The synthetic procedure was the same as that of Compound 48.

$^1$H-NMR (500 MHz, CDCl$_3$) δ 8.14-8.10 (m, 2H), 7.62-7.56 (m, 1H), 7.50-7.39 (t, 2H, J=8.0 Hz), 6.00-5.91 (m, 1H), 5.49 (dd, 1H, $J_1$=3.5 Hz, $J_2$=11.0 Hz), 5.42-4.80 (m, 3H), 5.25 (dd, 1H, $J_1$=1.5 Hz, $J_2$=10.5 Hz), 5.22 (d, 1H, J=10.0 Hz, NHAc), 5.11 (d, 1H, J=3.5 Hz, anomeric H of GalNAc), 4.88 (ddd, 1H, $J_1$=4.5 Hz, $J_2$=9.5 Hz, $J_3$=12.0 Hz), 4.38 (dd, 1H, $J_1$=2.0 Hz, $J_2$=12.5 Hz), 4.36-4.33 (m, 1H), 4.28 (ddt, 1H, $J_1$=$J_2$=1.5 Hz, $J_3$=5.0 Hz, $J_4$=13.0 Hz), 4.13-3.97 (m, 6H), 3.87 (dd, 1H, $J_1$=5.5 Hz, $J_2$=9.5 Hz), 3.81 (s, 3H, COOMe), 3.78 (dd, 1H, $J_1$=7.0 Hz, $J_2$=9.5 Hz), 3.20 (d, 1H, J=4.5 Hz, OH), 2.57 (dd, 1H, $J_1$=4.5 Hz, $J_2$=13.0 Hz, sialH-3 eq), 2.12 (s, 3H, OAc), 2.10 (s, 3H, OAc), 2.03 (s, 3H, OAc), 2.02 (t, 1H, $J_1$=$J_2$=12.5 Hz sialH-3ax), 1.91 (s, 3H, OAc), 1.87 (s, 3H, NAc); $^{13}$C-NMR (75 MHz, CDCl$_3$) δ 171.00, 170.86, 170.45, 170.29, 170.11, 167.96, 165.66, 133.29, 133.15, 129.89, 129.46, 128.35, 117.85, 98.54, 97.13, 72.76, 71.55, 69.36, 68.91, 68.55, 68.45, 67.32, 66.78, 62.77, 62.54, 57.60, 52.98, 49.07, 36.70, 23.00, 20.97, 20.73, 20.66, 20.48; HRMS (m/z): [M+Na]$^+$ calcd. for [C$_{36}$H$_{46}$N$_4$NaO$_{18}$]$^+$, 845.2699. found, 845.2690

Embodiment 46 Synthesis of Compound 60 and 53

Compound 56 (For its synthesis, see Tetrahedron Lett. 2005, 46, 8993-8995)(7.91 g, 21.2 mmol) was dissolved in CH$_2$Cl$_2$ (66 mL), and AllylOH (7.0 mL, 102 mmol) and BF$_3$.Et$_2$O (25 mL, 197.5 mmol) was added. The mixture was heated under reflux for 3 h. BF$_3$.Et$_2$O (10 mL, 79 mmol) was added and the mixture was refluxed for another 3 h. The solvent was evaporated under reduced pressure, and the residue was neutralized with saturated KHCO$_3$ aq. The mixture was extracted with ethyl acetate (150 mL×3). The organic layer were collected, dried over anhydrous Na$_2$SO$_4$, and concentrated in vacuum. The residue was purified by column chromatography on silica gel (acetone:petroleum ether=1:6) to afford 57 (5.68 g). The anomeric isomers could not be separated, and were employed for the following reaction without further purification.

To a stirred solution of the above product 57 (4.82 g, 13.0 mmol) in methanol (70 mL) was added a sodium methoxide solution in methanol (30%, 0.5 g, 2.78 mmol). The mixture was stirred at R.T. for 0.5 h. The reaction mixture was neutralized with strongly acidic resin, which was filtered off later. The solvent was removed under reduced pressure to afford 58 (2.88 g, yield=91%).

To a solution of the above product 58 (2.88 g, 11.75 mmol) in MeCN (10 mL) was added PhCH(OMe)$_2$ (2.15 g, 14.13 mmol) and CSA (203 mg, 0.88 mmol). The mixture was stirred at R.T. for 18 h. After triethylamine (0.2 g, 2.0 mmol) was added, the mixture was concentrated under reduced pressure. The residue was purified by column chromatography on silica gel to afford 59 (2.78 g). The unstable α isomer was separated in this stage. The product employed for the following reaction was without complete purification.

The above product 59 (2.78 g, 8.35 mmol) and DMAP (70 mg, 0.6 mmol) were dissolved in pyridine (10 mL), and the solution was cooled on ice bath. BzCl (1.8 mL, 15 mmol) was added dropwise. The mixture was stirred at R.T. for 24 h. The solvent was evaporated under reduced pressure. The residue was neutralized with saturated KHCO$_3$ aq., and extracted with ethyl acetate (150 mL×3). The organic layer were collected, dried over Na$_2$SO$_4$, and concentrated under reduced pressure. The residue was purified by column chromatography on silica gel (acetone:petroleum ether=1:5) to afford 60 (3.21 g, yield=88%).

Compound 60: $^1$H-NMR (300 MHz, CDCl3) δ 8.14-8.07 (m, 2H), 7.63-7.55 (m, 1H), 7.48-7.43 (m, 4H), 7.37-7.33 (m. 3H), 6.02-5.95 (m, 1H), 5.60 (dd, 1H, J1=3.6 Hz, J2=11.1 Hz, H-3), 5.55 (s, 1H), 5.37 (dq, 1H, J1=1.5 Hz, 17.1 Hz, terminal H of vinyl in allyl), 5.26 (dd, 1H, J1=1.5 Hz, J2=10.2 Hz, terminal H of vinyl in allyl), 5.19 (d, 1H, J=3.0 Hz, anomeric H), 4.63 (d, 1H, J=2.7 Hz), 4.29 (dd, 1H, J1=2.5 Hz, J2=12.3 Hz, H-6a), 4.28 (ddt, 1H, J1=J2=1.5 Hz, J3=5.4 Hz, J4=13.0 Hz, —OCH2 in allyl), 4.16-4.08 (m, 3H), 3.90-3.86 (br, 1H), 13C-NMR (75 MHz, CDCl3) δ 171.89, 165.95, 137.44, 133.68, 133.44, 133.04, 130.13, 129.90, 129.29, 128.89, 128.74, 128.44, 128.08, 125.96, 118.20, 100.48, 97.50, 73.51, 70.05, 69.07, 68.83, 62.67, 57.53; HRMS (m/z): [M+Na]$^+$ calcd. for [C$_{23}$H$_{23}$N$_3$NaO$_6$]$^+$, 460.1479. found, 460.1488.

To a solution of Compound 60 (688 mg, 1.57 mmol, For its synthesis, see the foregoing two paragraphs) in MeOH (10 mL) was added strongly acidic resin (668 mg). The mixture was stirred at 40° C. for 4 h. The resin was filtered off, and the solvent was removed under reduced pressure. The residue was purified by column chromatography on silica gel (acetone:petroleum ether=1:3) to afford 53 (402 mg, yield=73%):

Compound 53: $^1$H-NMR (500 MHz, CDCl$_3$) δ 8.09-8.05 (m, 2H), 7.60-7.55 (m, 1H), 7.46-7.42 (m, 2H), 5.97-5.88 (m, 1H), 5.45 (dd, 1H, J1=3.0 Hz, J2=11.0 Hz, H-3), 5.34 (dq, 1H, J1=1.5 Hz, J2=17.5 Hz, terminal H of vinyl in allyl), 5.24 (dq, 1H, J=1.5 Hz, J2=10.0 Hz, terminal H of vinyl in allyl), 5.08 (d, 1H, J=3.5 Hz, anomeric H), 4.39 (d, 1H, J=2.5 Hz, H-4), 4.22 (ddt, 1H, J1=J2=1.5 Hz, J3=6.5 Hz, J4=13.0 Hz, —OCH2 in allyl), 4.05 (ddt, 1H, J1=J2=1.5 Hz, J3=6.5 Hz, J4=13.0 Hz, —OCH2 in allyl), 4.00-3.94 (m, 2H), 3.91-3.81 (m, 2H), 3.55 (br, 1H, OH), 2.93 (br, 1H, OH); 13C-NMR (75 MHz, CDCl3) δ 165.74, 133.55, 133.04, 129.81, 129.10, 128.49, 118.03, 97.28, 71.61, 69.14, 68.73, 62.85, 57.45; HRMS (m/z): [M+Na]$^+$ calcd. for [C$_{16}$H$_{19}$N$_3$NaO$_6$]$^+$, 372.1166. found, 372.1158

Embodiment 47 Synthesis of Compound 61

This compound was prepared from Compound 47 and 62 (See *Carbohydr. Res.* 1994, 253, 167-183), affording 61 (yield=51%). The synthetic procedure was the same as that of Compound 48.

Compound 61: $^1$H-NMR (500 MHz, D$_2$O) δ 8.05-7.98 (m, 4H), 7.53-7.48 (m, 2H), 7.40-7.35 (m, 4H), 5.90-5.81 (m, 1H), 5.73-5.67 (m, 2H), 5.40-5.26 (m, 5H), 5.16-5.12 (m, 1H), 4.90 (ddd, 1H, J1=4.5 Hz, J2=9.5 Hz, J3=11.5 Hz), 4.41-4.37 (m, 2H), 4.25 (ddt, 1H, J1=J2=1.5 Hz, J3=5.5 Hz, J4=13.5 Hz), 4.18 (t, 1H, J1=J2=6.0 Hz), 4.16-4.02 (m, 4H), 3.92 (dd, 1H, J1=5.5 Hz, J2=9.5 Hz), 3.82 (s, 3H, COOMe, overlapped), 3.84-3.80 (m, 1H, overlapped), 3.12 (b, 1H, OH), 2.59 (dd, 1H, J1=5.0 Hz, J2=13.0 Hz, sialH-3 eq), 2.14 (s, 3H, OAc), 2.11 (s, 3H, OAc), 2.03 (s, 3H, OAc), 2.02 (t, 1H, J1=J2=12.5 Hz sialH-3ax), 1.94 (s, 3H, OAc), 1.88 (s, 3H, NAc); 13C-NMR (125 MHz, CDCl3) δ 170.93, 170.27, 170.23, 170.19, 168.05, 165.99, 165.92, 133.57, 133.12, 129.79, 129.77, 129.66, 129.52, 128.33, 117.38, 98.70, 95.73, (77.25, 77.00, 76.74 CDCl3), 72.85, 71.13, 69.24, 68.96, 68.87, 68.51, 68.22, 67.65, 67.40, 62.93, 62.57, 53.03, 49.35, 36.98, 23.14, 21.04, 20.81, 20.76, 20.54; HRMS (m/z): [M+Na]$^+$ calcd. for [C$_{43}$H$_{51}$NNaO$_{20}$]$^+$, 924.2897. found, 924.2905

Embodiment 48 Synthesis of Compound 63

This compound was prepared from Compound 47 and 64 (See *Monatshefte fuer Chemie.* 2002, 133, 531-540), affording 63 (yield=51%). The synthetic procedure was the same as that of Compound 48.

Compound 63: $^1$H-NMR (500 MHz, D$_2$O) δ 8.06-8.03 (m, 2H), 7.58-7.53 (m, 1H), 7.45-7.41 (m, 2H), 5.94-5.85 (m, 2H), 5.49-5.41 (m, 2H), 5.35-5.21 (m, 4H), 5.05-4.97 (m, 1H), 4.92 (d, 1H, J=4.0 Hz, anomeric H on GlcNAc), 4.45 (ddd, 1H, J1=4.0 Hz, J2=10.0 Hz, J3=11.0 Hz), 4.29-4.22 (m, 2H), 4.25 (ddt, 1H, J1=J2=1.5 Hz, J3=5.5 Hz, J4=12.5 Hz), 4.14 (dd, 1H, J1=1.5 Hz, J2=10.5 Hz), 4.10-3.96 (m, 4H), 3.81 (s, 3H, COOMe), 3.83-3.78 (1H, overlapped), 3.76 (dd, 1H, J1=1.5 Hz, J2=11.2 Hz), 3.44 (br., 1H, OH), 2.66 (dd, 1H, J1=5.0 Hz, J2=13.5 Hz, sialH-3 eq), 2.11 (s, 3H, OAc), 1.90-1.80 (1H, sial H-3ax, overlapped), 2.06 (s, 3H, OAc), 2.00 (s, 3H, OAc), 1.90 (s, 3H, OAc), 1.86 (s, 3H, NAc), 1.84 (s, 3H, NAc); 13C-NMR (125 MHz, CDCl3) δ 170.99, 170.60, 170.34, 170.05, 169.98, 169.56, 168.24, 167.34, 133.34, 133.22, 129.80, 129.58, 128.36, 118.00, 97.86, 96.74, 73.80, 72.22, 71.16, 68.85, 68.49, 68.37, 68.01, 67.11, 62.76, 62.18, 52.87, 51.86, 49.59, 37.77, 23.13, 23.09, 21.02, 20.87, 20.65, 20.27; HRMS (m/z): [M+Na]$^+$ calcd. for C$_{38}$H$_{50}$N$_2$NaO$_{19}$, 861.2900. found, 861.2872

Embodiment 49 Synthesis of Glycoconjugates by Conjugation Reaction between Hapten 2-14, 16-24, 29-34, 42 and Carrier Protein/Peptide The hapten (Compound 2, 10 mg) was dissolved in anhydrous methanol (2 mL). At −78° C., ozone was introduced into the mixture. When the color of the mixture turned blue (about 10~30 min), the ozone was cut out. The color stayed blue for about 10 min. N$_2$ was then introduced into the flask to extrude the ozone in excess. Dimethylsulfide (0.5 mL) was added dropwise. The temperature was allowed to R.T. spontaneously. After 2 h, the solvent was removed in vacuum, affording the aldehyde derivative. The aldehyde derivative of the carbohydrate hapten and the protein (or polypeptide), such as BSA or KLH (10 mg), were dissolved in pH 7.2 buffer. NaBH$_3$CN (3 mg) was added. The reaction flask was placed on a shaking table and the mixture was shaken for 24 h. The mixture was dialyzed to afford the desired glycoconjugate STn-KLH.

According to aforementioned procedure, the compounds of Embodiment 3-47 (2-14, 16-24, 29-34, 42) are conjugated to the protein carrier to afford the corresponding glycoconjugates 3-KLH, 4-KLH, 5-KLH, 6-KLH, 7-KLH, 8-KLH, 9-KLH, 10-KLH, 11-KLH, 12-KLH, 14-KLH, 16-KLH, 17-KLH, 18-KLH, 19-KLH, 20-KLH, 21-KLH, 22-KLH, 23-KLH, 24-KLH, 29-KLH, 30-KLH, 31-KLH, 32-KLH, 33-KLH, 34-KLH, 42-KLH.

It should be noted that although the structurally typical $R_1$, $R_2$, $R_3$, $R_4$, $R_5$ and $R_6$ have been employed in the syntheses of STn derivatives and their conjugates with proteins (or polypeptides), the art described in the present invention can be applied to syntheses of structurally diverse R substituents, with $R_1$ being any acylamino, $-NH_2$, $-N_3$ or $-OH$ group; $R_2$ any acylamino, $-NH_2$, $-N_3$, $-OH$ group; $R_3$ equatorial or axial $-CO_2H$, $-CH_2OH$, $-CO_2M$, $-C(O)NHOH$, $-H$ wherein M may be alkyl, aryl, heterocycle or cation); $R_4$ different linkers; $R_5$ equatorial or axial $-OH$; and R6 H or β-galactosyl. These synthetic tasks can be accomplished without any creative endeavor by the person in the art. It is obvious that the scope of the patent protection is not constrained with the limited compounds of the presented Embodiments.

Characterizing the Immune Response

1. Materials and resources:
Test antigens: glycoproteins (or -polypeptides) prepared in Embodiment 49 of the present invention.

2. Test method:
(1) Immunization of mice
Groups of six mice (female pathogen-free BALB/c, age 6-8 weeks, Number: SCXKjing2007-0001, SPF/VAF, from Department of Laboratory Animal Science, Peking University Health Science Center) were immunized four times at 2-week intervals with STn-KLH or modified STn-KLH glycoconjugates (each containing 2 μg of carbohydrate in PBS). The vaccines were administered intraperitoneally. Mice were bled prior to the initial vaccination, 13 days after the second and the third vaccinations, and 14 days after the fourth vaccination. Blood was clotted to obtain sera, which were stored at −80° C.

(2) Serological assays.
The total antigen-specific antibody titers of the pooled sera were assessed by means of ELISA.
1 ELISA plate was coated with 100 μL of STn-BSA (including 0.02 μg of STn) overnight at 4° C. (0.1 M bicarbonate buffer, pH=9.6).
2 After being washed three times (200 μL per time for per microwell) with PBS-Tween20 (0.05%), microwells were blocked with 3% BSA-PBS (200 μL per microwell) and incubated for 1 h at 37° C.
3 After the plate was washed for three times, serially diluted sera (1% BSA-PBS, double diluted) were added to microwells (100 μL/well) and incubated for 1 h at 37° C.
4 The plate was washed for three times and incubated with 1:5000 dilution of horseradish peroxidase-conjugated goat anti-mouse IgG (γ-chain specific) or IgM (μ-chain specific) (Southern Biotechnology Associates, Inc., Buckingham, Ala.) for 1 h at 37° C.
5 The plate was washed for three times, developed with o-phenylenediamine (OPD) substrate in the dark for 15 min terminated by addition of 2M $H_2SO_4$.
6 The OD value is read at 490 nm on the Microplate reader. The antibody titer was defined as the highest dilution showing an absorbance of 0.1, after subtracting background.

(3) Result
1)

TABLE 1

Table 1. ELISA titers anti-STn 13 days after the second vaccination

| Group | IgG | IgM |
|---|---|---|
| immunized with STn-KLH | 910 | <1000 |
| immunized with 3-KLH | <1000 | <1000 |
| immunized with 4-KLH | <1000 | <1000 |
| immunized with 5-KLH | <1000 | <1000 |
| immunized with 6-KLH | <1000 | <1000 |
| immunized with 7-KLH | <1000 | <1000 |
| immunized with 8-KLH | 7734 | <1000 |
| immunized with 9-KLH | <1000 | <1000 |
| immunized with 10-KLH | 7933 | <1000 |
| immunized with 11-KLH | <1000 | <1000 |
| immunized with 12-KLH | <1000 | <1000 |
| immunized with 13-KLH | <1000 | <1000 |
| immunized with 14-KLH | <1000 | <1000 |
| immunized with 16-KLH | <1000 | <1000 |
| immunized with 17-KLH | <1000 | <1000 |
| immunized with 18-KLH | 1381 | <1000 |
| immunized with 19-KLH | <1000 | <1000 |
| immunized with 20-KLH | 11000 | <1000 |
| immunized with 21-KLH | 1266 | <1000 |
| immunized with 22-KLH | <1000 | <1000 |
| immunized with 23-KLH | <1000 | <1000 |
| immunized with 24-KLH | 6618 | <1000 |
| immunized with 29-KLH | <1000 | <1000 |
| immunized with 30-KLH | <1000 | <1000 |
| immunized with 31-KLH | 20000 | <1000 |
| immunized with 32-KLH | <1000 | <1000 |
| immunized with 33-KLH | <1000 | <1000 |
| immunized with 34-KLH | <1000 | <1000 |
| immunized with 42-KLH | <1000 | <1000 |

2)

TABLE 2

ELISA titers anti-STn 13 days after the third vaccination

| Group | IgG | IgM |
|---|---|---|
| immunized with STn-KLH | 50,144 | 5763 |
| immunized with 3-KLH | <2500 | <1000 |
| immunized with 4-KLH | 17,040 | 1604 |
| immunized with 5-KLH | 38,878 | 1872 |
| immunized with 6-KLH | <2500 | <1000 |
| immunized with 7-KLH | 23,279 | 4706 |
| immunized with 8-KLH | 43,201 | 4963 |
| immunized with 9-KLH | 4714 | 2897 |
| immunized with 10-KLH | 55,004 | <1000 |
| immunized with 11-KLH | 4054 | <1000 |
| immunized with 12-KLH | 11,783 | <1000 |
| immunized with 13-KLH | 24,512 | <1000 |
| immunized with 14-KLH | <2500 | <1000 |
| immunized with 16-KLH | <2500 | 2571 |
| immunized with 17-KLH | 11,329 | 2047 |
| immunized with 18-KLH | 56,276 | 1842 |
| immunized with 19-KLH | <2500 | <1000 |
| immunized with 20-KLH | 185,354 | 2581 |
| immunized with 21-KLH | 150,504 | 9236 |
| immunized with 22-KLH | 24,154 | 1586 |
| immunized with 23-KLH | 38,173 | 2880 |
| immunized with 24-KLH | 93,488 | <1000 |
| immunized with 29-KLH | <2500 | 1979 |
| immunized with 30-KLH | <2500 | <1000 |
| immunized with 31-KLH | 276,162 | 1804 |
| immunized with 32-KLH | <2500 | <1000 |
| immunized with 33-KLH | <2500 | <1000 |

TABLE 2-continued

ELISA titers anti-STn 13 days after the third vaccination

| Group | IgG | IgM |
| --- | --- | --- |
| immunized with 34-KLH | 6108 | <1000 |
| immunized with 42-KLH | <2500 | <1000 |

3)

TABLE 3

IgG antibody titer anti-STn of individual mouse immunized with 20-KLH, 21-KLH, 31-KLH and 2-KLH after the 3rd vaccination

| | STn-KLH | 20-KLH | 31-KLH | 21-KLH |
| --- | --- | --- | --- | --- |
| Mouse 1 | 5,170 | 296,647 | 179,666 | 24,235 |
| Mouse 2 | 6,385 | 79,799 | 356,282 | 182,259 |
| Mouse 3 | 65,524 | 283,403 | 291,807 | 71,044 |
| Mouse 4 | 96,812 | 63,561 | 83,396 | 85,645 |
| Mouse 5 | 6,187 | 69,508 | 104,519 | 89,172 |
| Mouse 6 | 18,663 | 68,401 | 351,977 | 472,834 |

Figure 5:
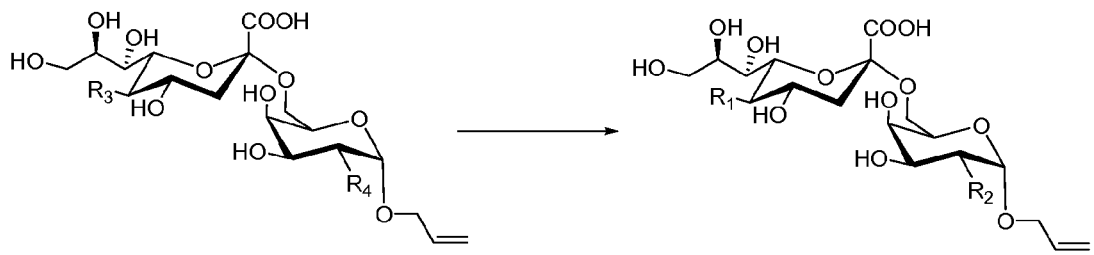
FIG. 5 shows the routes of N-acylation; (i) carboxylic anhydride, MeOH, $NaHCO_3$; or (2) carboxylic ester, TEA, MeOH; carboxylic acid, HBTU, DMF.
Figure 6:
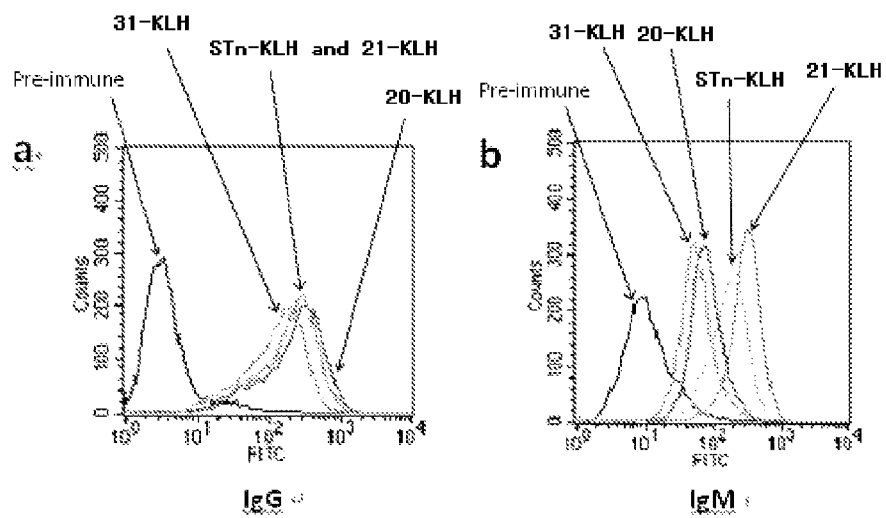
FIG. 6 shows the combination between the mice sera and the tumor cells 13th days after $3^{rd}$ vaccination of mice with the synthetic glycoconjugates.

4) The combination between the mice sera and the tumor cells 13 days after the $3^{rd}$ vaccination The result is shown in FIG. 5.

5) Result analysis

The data of titers were dealt with logarithmic function to base 10 and after transformation the data satisfied conditions of ANOVA. The F test is significant (F=5.18, p=0.0082). Dunnett's t Tests was used in multiple comparisons. The results indicated that the IgG levels for the conjugates of compounds 20, 21 and 31 exhibited a remarkable increase relative to 2 after the 4th immunizations and the difference was statistically significant ($\alpha$=0.05). The statistical analysis was performed with SAS software (version 9.1).

In vivo test of the effect of the synthetic glycoconjugates on killing tumor cells was not conducted. However, it is reported that (See *British J. Cancer* 2009, 100, 1746-1754) the anti-STn antibody (obtained after immunizing the mice) indeed represses tumor growth. Since higher titers of antibody were obtained in the present invention, it is expected that the repressive activity of the synthetic glycoconjugates surpasses that of the unmodified STn-KLH.

The invention claimed is:

1. A sialic acid ($\alpha$-(2→6))-D-aminopyranose derivative or salt of the following Formula (1):

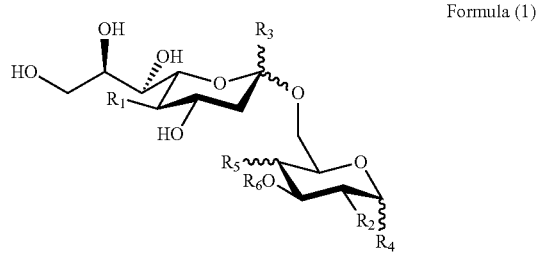

Formula (1)

wherein $R_1$ is independently selected from the group consisting of —NHC(O)CH$_x$Cl$_y$, —NHC(O)CH$_x$F$_y$, —NHC(O)CH$_x$Br$_y$, —NHC(O)H, —NHC(O)C$_a$H$_{2a+1}$, —NHC(O)C$_a$H$_{2a}$OH, —NHC(O)C$_b$H$_{2b-1}$, and —NHC(O)C$_b$H$_{2b-3}$, —NH$_2$, —N$_3$, and —OH, where x and y is 0, 1, 2, or 3, and the sum of x and y is 3; a is an integer between 1 and 20; and b is an integer between 2 and 20;

$R_2$ is independently selected from the group consisting of —NHC(O)CH$_p$Cl$_q$, —NHC(O)CH$_p$F$_q$, —NHC(O)CH$_p$Br$_q$, —NHC(O)H, —NHC(O)C$_a$H$_{2a+1}$, —NHC(O)C$_a$H$_{2a}$OH, —NHC(O)C$_b$H$_{2b-1}$, —NHC(O)C$_b$H$_{2b-3}$, acylamino, —NH$_2$, —N$_3$, and —OH, where p and q is 0, 1, 2 or 3, and the sum of p and q is 3; a is an integer between 1 and 20; and b is an integer between 2 and 20;

$R_1$ and $R_2$ are not —NHC(O)CH$_3$ simultaneously;

$R_3$ is independently selected from the group consisting of —CO$_2$H, —CH$_2$OH, —CO$_2$M, C(O)NHOH and hydrogen, where M is alkyl, aryl or heteroaryl, and the orientation of the $R_3$ is an equatorial bond or an axial bond;

$R_4$ is allyloxy;

$R_5$ is —OH, and the orientation of the $R_5$ is an equatorial bond or an axial bond; and $R_6$ is Hydrogen or $\beta$-galactosyl-.

2. A glycoconjugate characterized by conjugating the sialic acid-$\alpha$-(2→6)-D-aminopyranose derivative or salt of claim 1 to a protein or a polypeptide.

3. The sialic acid ($\alpha$-(2→6))-D-aminopyranose derivative or salt claim 1, wherein the sialic acid ($\alpha$-(2→6))-D-aminopyranose derivative or salt is characterized in that the salt is formed with a base.

4. A process of preparing the sialic acid ($\alpha$-(2→6))-D-aminopyranose derivative or salt of the following Formula (1), the process comprising: an acylation reaction in a solvent with carboxylic acid anhydrides, carboxylic acids or carboxylic esters in the presence of a reaction promoter, and using a sialic acid with 5-naked amino- and/or aminogalactose (aminoglucose) with 2-naked amino- as raw materials;

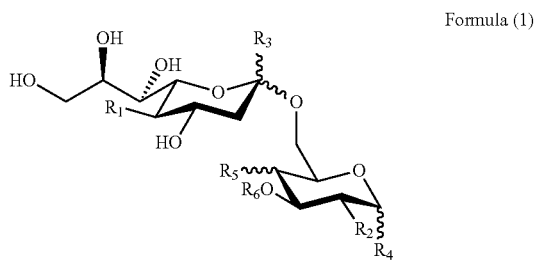

Formula (1)

wherein $R_1$ is independently selected from the group consisting of —NHC(O)CH$_x$Cl$_y$, —NHC(O)CH$_x$F$_y$, —NHC(O)CH$_x$Br$_y$, —NHC(O)H, —NHC(O)C$_a$H$_{2a+1}$, —NHC(O)C$_a$H$_{2a}$OH, —NHC(O)C$_b$H$_{2b-1}$, and —NHC(O)C$_b$H$_{2b-3}$, —NH$_2$, —N$_3$, and —OH; where x and y is 0, 1, 2 or 3, and the sum of x and y is 3; a is an integer between 1 and 20; and b is an integer between 2 and 20;

$R_2$ is independently selected from the group consisting of —NHC(O)CH$_p$Cl$_q$, —NHC(O)CH$_p$F$_q$, —NHC(O)CH$_p$Br$_q$, —NHC(O)H , —NHC(O)C$_a$H$_{2a+1}$, —NHC(O)C$_a$H$_{2a}$OH , —NHC(O)C$_b$H$_{2b-1}$, —NHC(O)C$_b$H$_{2b-3}$, —NH$_2$, —N$_3$, and —OH; where p and q is -0, 1, 2 or 3, and the sum of p and q is 3; a is an integer between 1 and 20; and b is an integer between 2 and 20;

$R_1$ and $R_2$ are not —NHC(O)CH$_3$ simultaneously;

$R_3$ is independently selected from the group consisting of —CO$_2$H, —CH$_2$OH, —CO$_2$M, C(O)NHOH and hydrogen, where M is alkyl, aryl or heteroaryl, and the orientation of the $R_3$ is an equatorial bond or an axial bond;

$R_4$ is allyloxy;

$R_5$ is —OH, and the orientation of the $R_5$ is an equatorial bond or an axial bond; and $R_6$ is Hydrogen or β-galactosyl-.

5. The Process of claim 4, wherein the preparation process is characterized in that the raw materials include allyl 4-O-(5-amino-3,5-dideoxy-α-neuraminopyranosyl)-2-acetylamino-2-deoxy-α-D-galactopyranoside, allyl 4-O-(5-acetylamino-3,5-dideoxy-α-neuraminopyranosyl)-2-amino-2-deoxy-α-D-galactopyranoside or allyl 4-O-(5-amino-3,5-dideoxy-α-neuraminopyranosyl)-2-amino-2-deoxy-α-D-galactopyranoside; the carboxylic acid anhydrides include aliphatic carboxylic acid anhydrides, with/without fluoro, chloro or bromo substituents; that the carboxylic acids include aliphatic acids, with/without fluoro, chloro or bromo substituents; that the carboxylic esters include aliphatic esters, with/without fluoro, chloro or bromo substituents; the promoter include organic or inorganic bases; and that the solvents include water or organic solvents.

6. The Process of claim 5, wherein the preparation process is characterized in that the carboxylic acid anhydrides include acetic anhydride, propionic anhydride, n-butyric anhydride, iso-butyric anhydride and caproic anhydride; the carboxylic acids include mono-, di- and trifluoroacetic acid and mono-, dichloroacetic acid; and that the esters include methyl mono-, di- and trifluoroacetate and methyl dichloroacetate.

7. A process of preparing a glycoconjugate, including (1) ozonization of the sialic acid (α-(2→6))-D-aminopyranose derivative or salt of claim 1 to give the corresponding disaccharide with aldehyde ; and (2) reductamination of the production obtained in step (1) with the carrier protein or polypeptide to give the conjugate.

8. A method of producing an anti-tumor drug, the method comprising preparing the sialic acid (α-(2→6))-D-aminopyranose derivative or salt of claim 1 to produce the anti-tumor drug.

9. A method of producing an anti-tumor drug, the method comprising preparing the glycoconjugate of claim 2 to produce the anti-tumor drug.

10. A method of treating a tumor, comprising:
administering to a subject in need thereof a composition comprising an effective dose the glycoconjugate of claim 2 and a pharmaceutically acceptable carrier or adjuvant.

* * * * *